(12) United States Patent
Kang et al.

(10) Patent No.: US 11,859,169 B2
(45) Date of Patent: *Jan. 2, 2024

(54) NANO-LIGAND FOR PROMOTING CELL ADHESION AND REGENERATION OF MACROPHAGES AND METHOD OF PROMOTING CELL ADHESION AND REGENERATION OF MACROPHAGES BY USING THE SAME

(71) Applicant: Korea University Research and Business Foundation, Seoul (KR)

(72) Inventors: Hee-Min Kang, Seoul (KR); Chandra Khatua, Seoul (KR); Gun-Hyu Bae, Hwaseong-si (KR); Hyo-Jun Choi, Seoul (KR); Sun-Hong Min, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 160 days.

This patent is subject to a terminal disclaimer.

(21) Appl. No.: 17/186,723

(22) Filed: Feb. 26, 2021

(65) Prior Publication Data

US 2021/0269773 A1 Sep. 2, 2021

(30) Foreign Application Priority Data

Feb. 28, 2020 (KR) .................. 10-2020-0025477
Apr. 24, 2020 (KR) .................. 10-2020-0050357

(51) Int. Cl.
*C12N 5/0786* (2010.01)
*A61K 9/51* (2006.01)
*C12N 13/00* (2006.01)

(52) U.S. Cl.
CPC .......... *C12N 5/0645* (2013.01); *A61K 9/5115* (2013.01); *A61K 9/5169* (2013.01); *C12N 13/00* (2013.01); *C12N 2501/998* (2013.01); *C12N 2529/00* (2013.01)

(58) Field of Classification Search
CPC .............................. C12N 5/0645; C12N 13/00; C12N 2501/998; C12N 2529/00; A61K 9/5115; A61K 9/5169
See application file for complete search history.

(56) References Cited

U.S. PATENT DOCUMENTS

2017/0285020 A1 10/2017 Mao et al.

OTHER PUBLICATIONS

Wong et al., Nano Lett. 2017, 17, 1685-1695 in view of Nature Communications, 2019, vol. 10, No. 1896 (Year: 2017).*
Nature Communications, 2019, vol. 10, No. 1896 (Year: 2019).*
Extended European Search Report dated Jul. 7, 2021 in Application No. 21159531.9.
Dexter S. H. Wong et al., "Magnetically Tuning Tether Mobility of Integrin Ligand Regulates Adhesion, Spreading, and Differentiation of Stem Cells", Nano Letters, Feb. 27, 2017, vol. 17, No. 3, pp. 1685-1695 (11 pages total).
Qui-Yun Chen et al., "Synthesis, characterization, cell imaging and anti-tumor activity of multifunctional nanoparticles", Spectrochimica Acta Part A: Molecular and Biomolecular Spectroscopy, May 3, 2012, vol. 96, pp. 284-288 (5 pages total).
Heemin Kang et al., "Immunoregulation of macrophages by dynamic ligand presentation via ligand-cation coordination", Nature Communications, Dec. 1, 2019, vol. 10, No. 1, retrieved from the internet, pp. 1-14, (14 pages total).
Hyojun Choi et al., "Remote Manipulation of Slidable Nano-Ligand Switch Regulates the Adhesion and Regenerative Polarization of Macrophages", Advanced Functional Materials, Aug. 1, 2020, vol. 30, No. 35, p. 2001446 (13 pages total).
Notice of Reasons for Refusal dated Feb. 22, 2022 from the Japanese Patent Office in Japanese Application No. 2021-031826.
Communication dated Nov. 15, 2022, issued in Japanese Application No. 2021-031826.

* cited by examiner

*Primary Examiner* — Robert S Cabral
(74) *Attorney, Agent, or Firm* — Sughrue Mion, PLLC

(57) ABSTRACT

The present invention relates to a nano-ligand for promoting cell adhesion and regeneration of macrophages and a method of promoting cell adhesion and regeneration of macrophages by using the nano-ligand. The method of promoting cell adhesion and regeneration of macrophages according to the present invention applies a magnetic field to a substrate including the nano-ligand, so that it is possible to reversely control the sliding of the nano-ligand, as well as temporally and spatially control the sliding of the nano-ligand, and efficiently control cell adhesion and phenotypic polarization of macrophages in vivo or ex vivo through the magnetic field-based spatiotemporal control.

6 Claims, 18 Drawing Sheets
(13 of 18 Drawing Sheet(s) Filed in Color)

[FIG. 1]
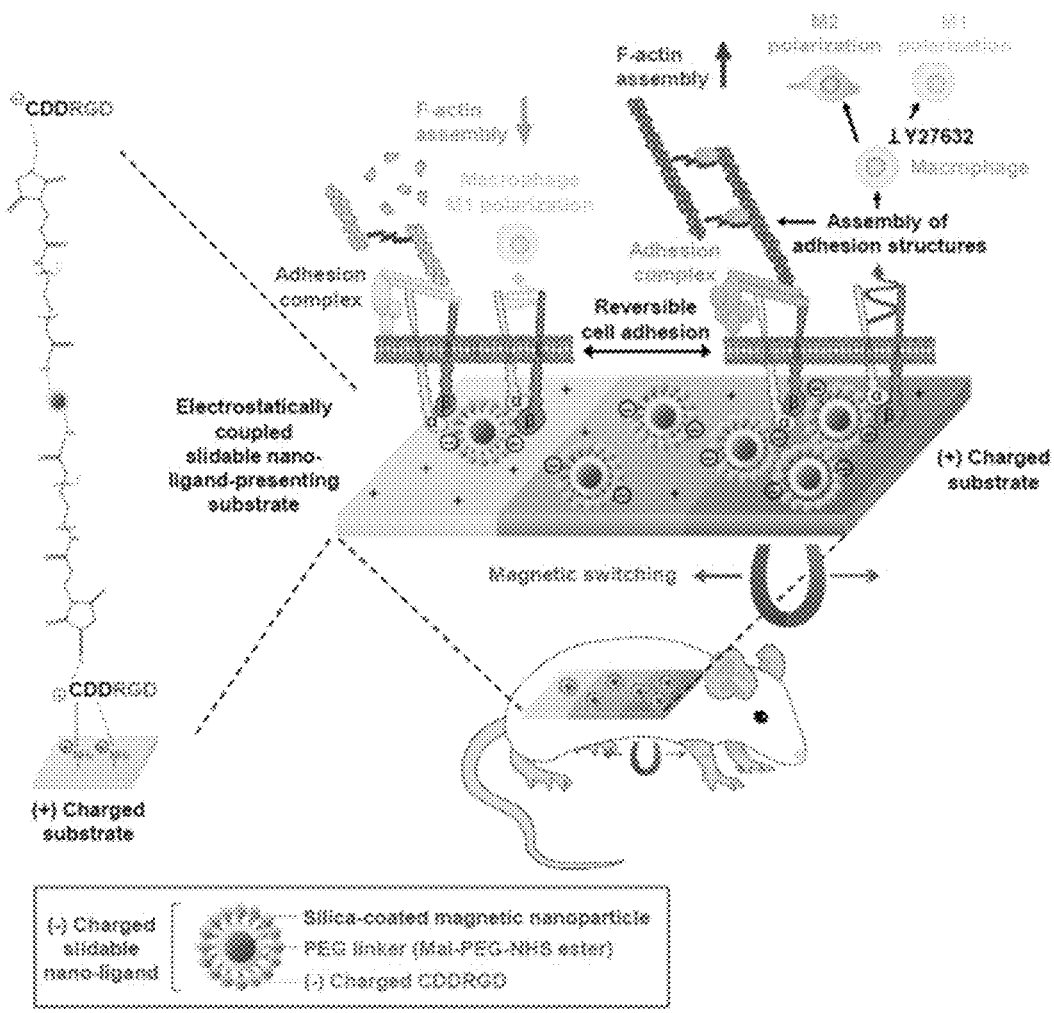

[FIG. 2]
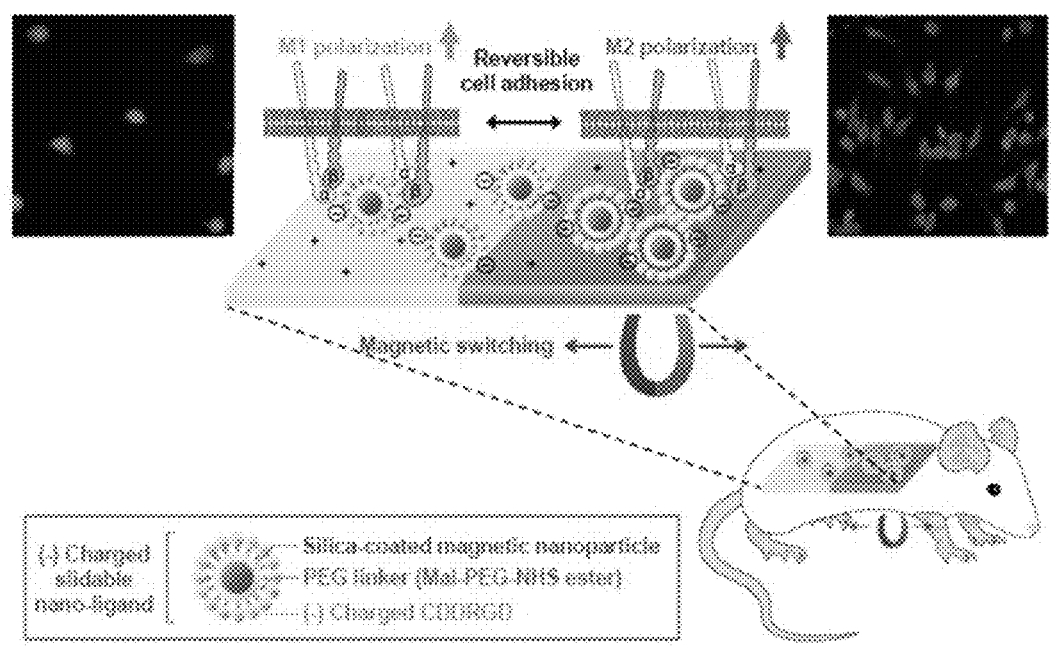
[FIG. 3]
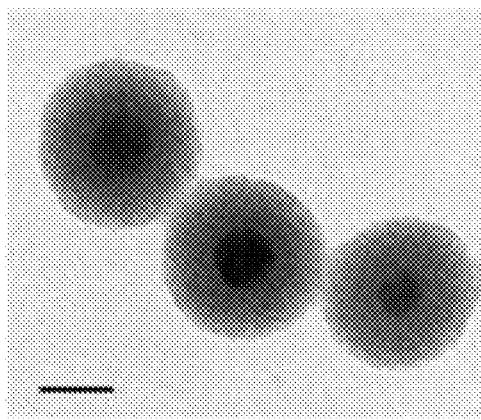

[FIG. 4]
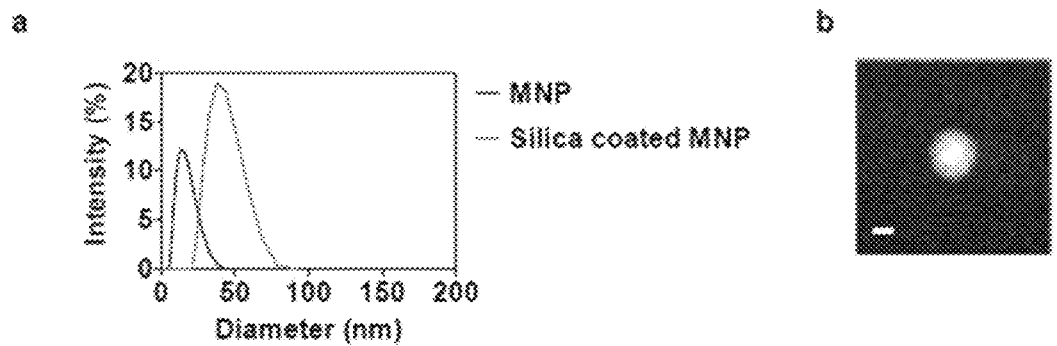
[FIG. 5]
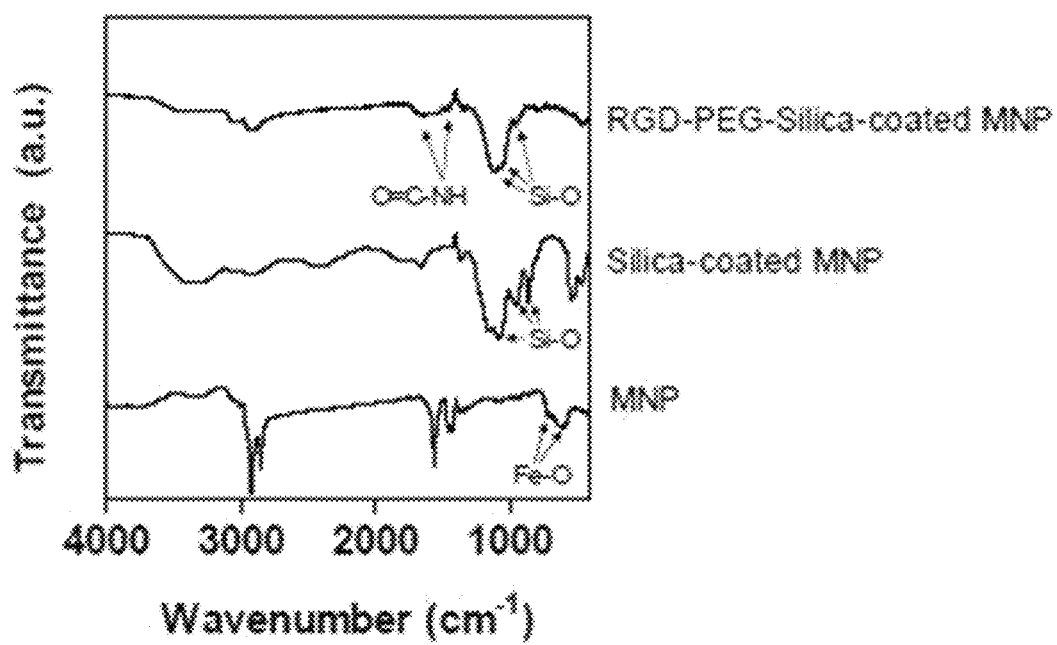

[FIG. 6]
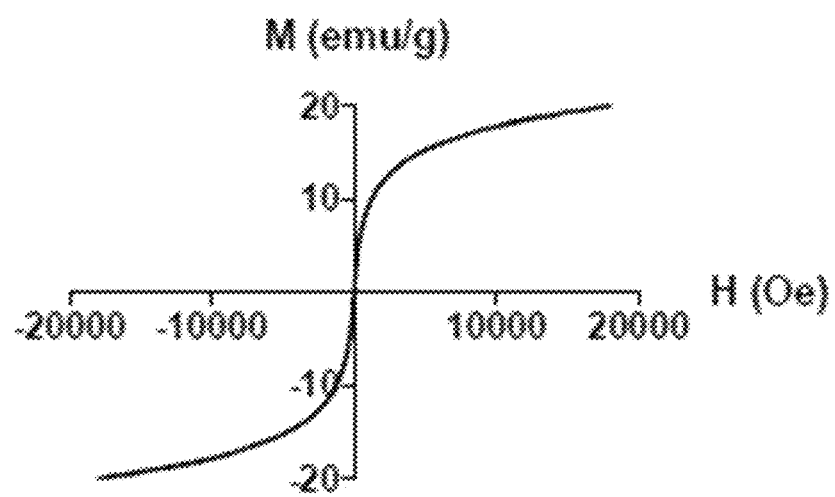

[FIG. 7]
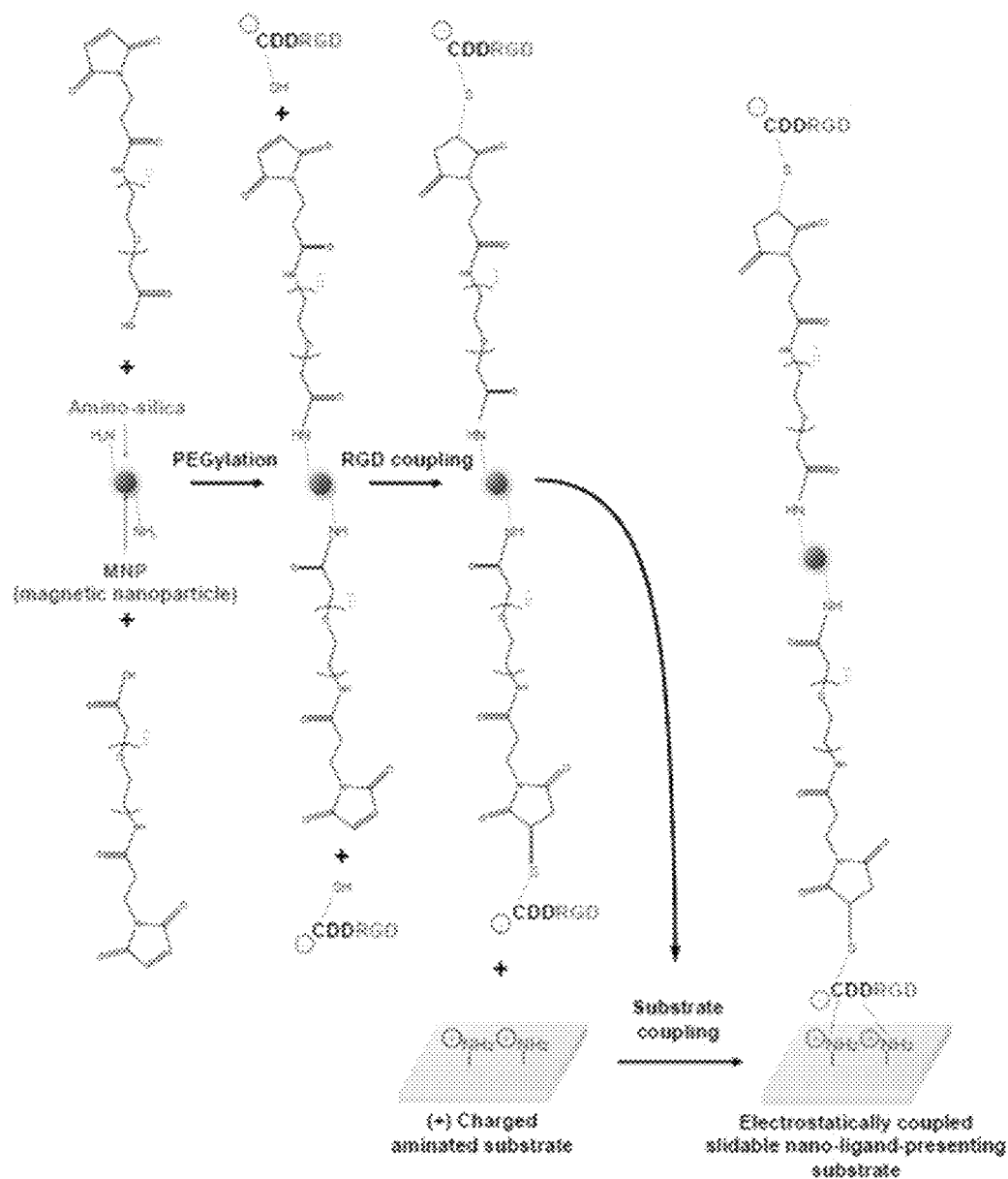

[FIG. 8]
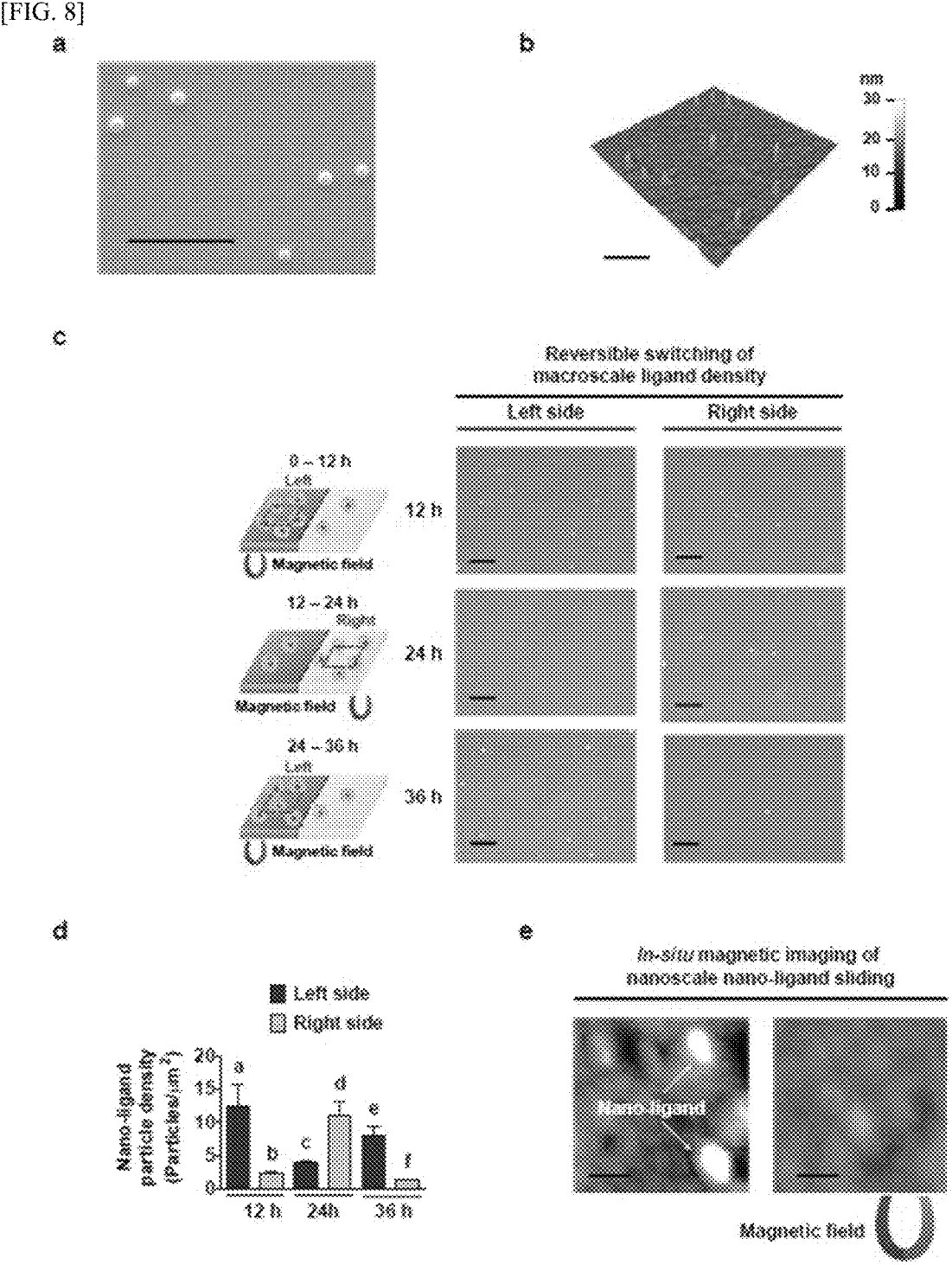

[FIG. 9]
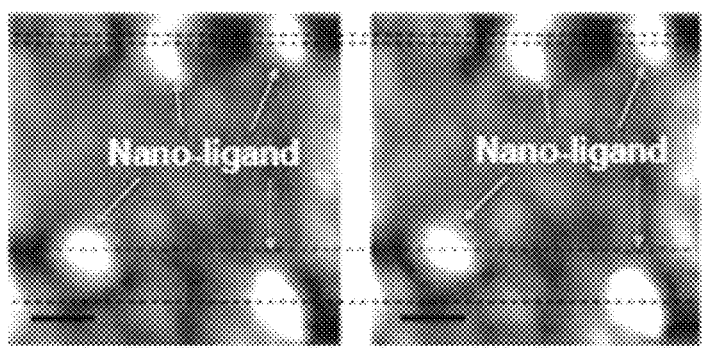
[FIG. 10]
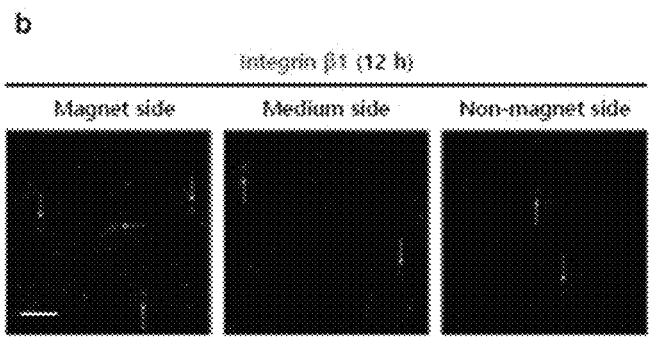
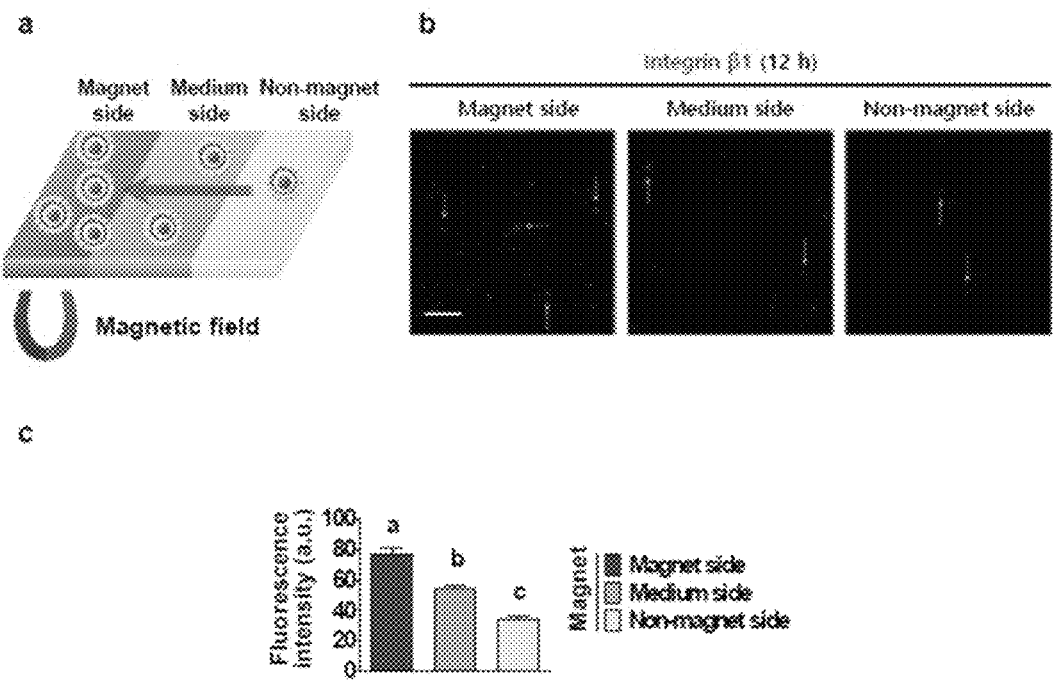

[FIG. 11]
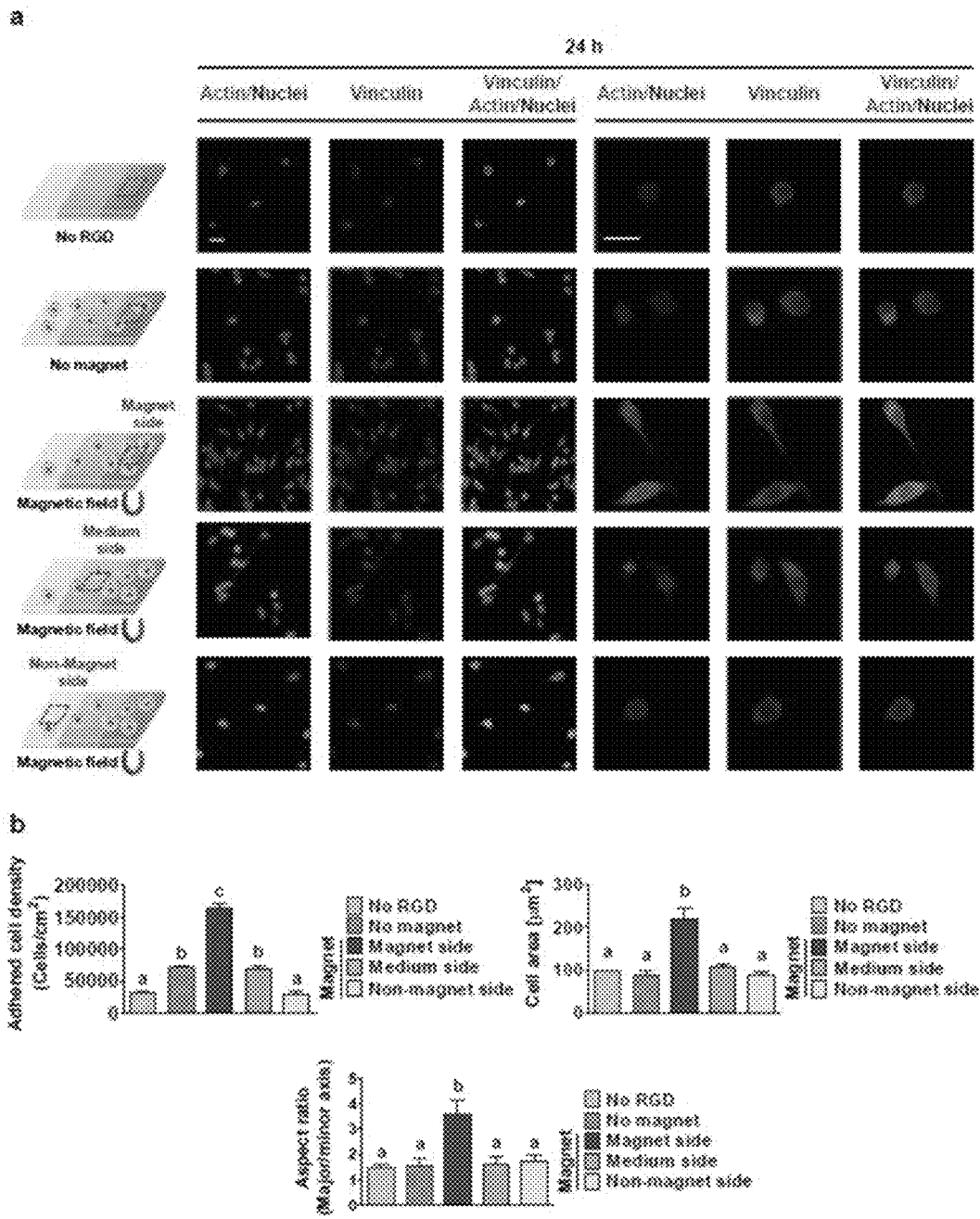

[FIG. 12]
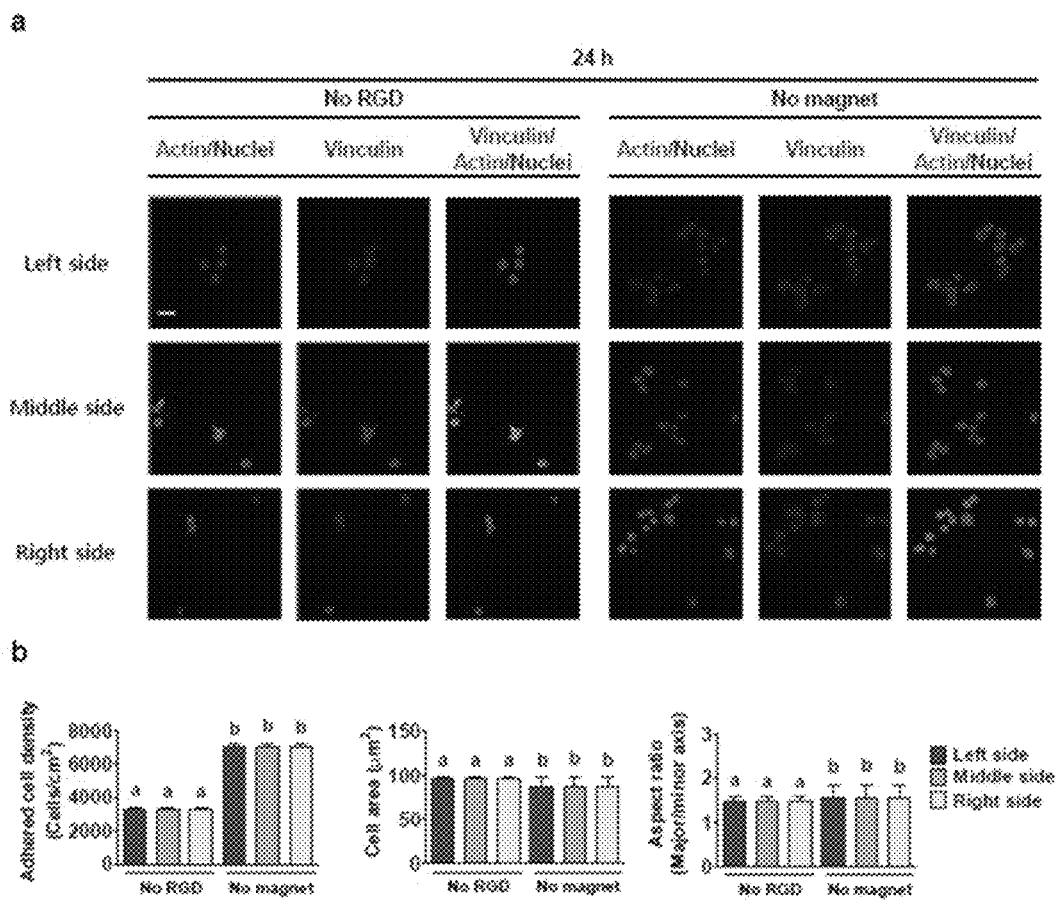

[FIG. 13]
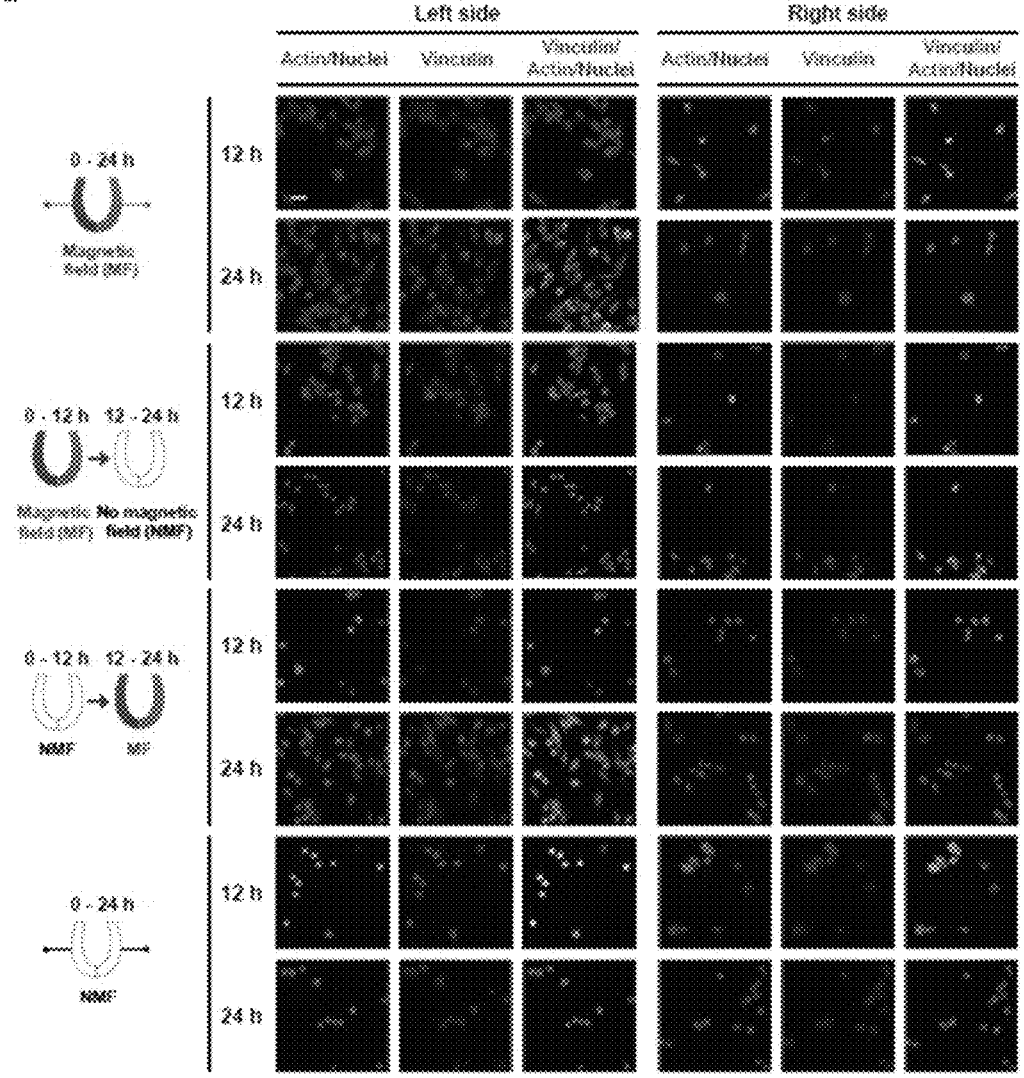
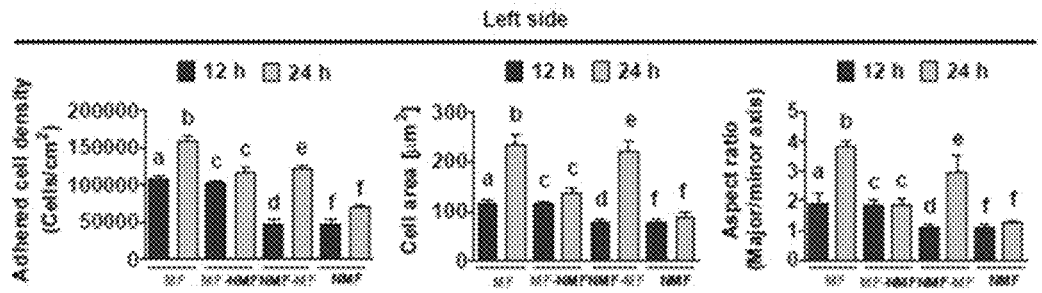

[FIG. 14]
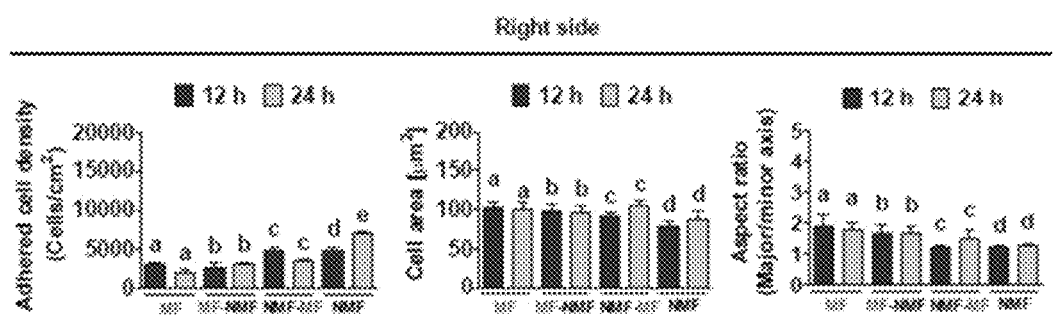

[FIG. 15]
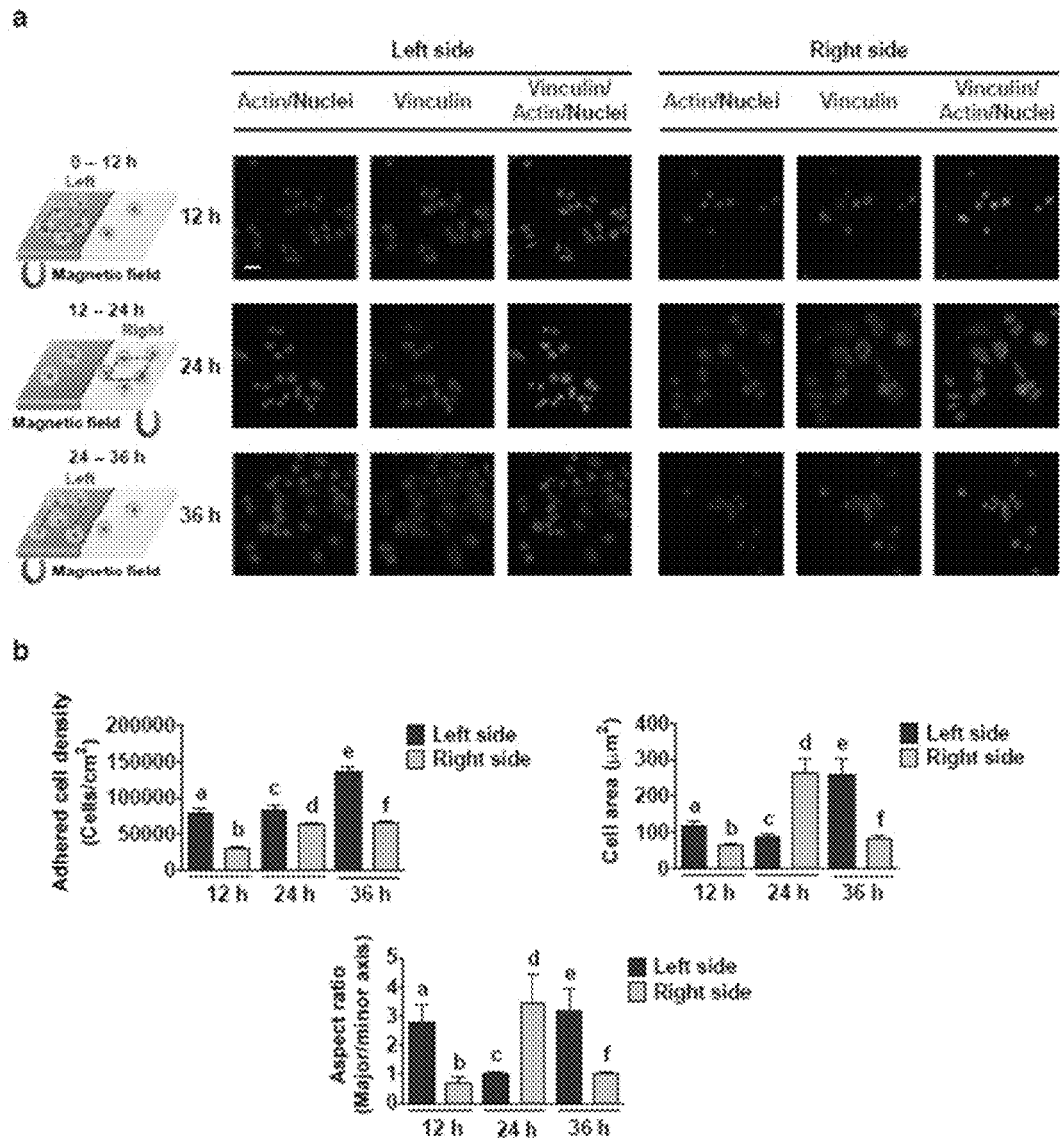

[FIG. 16]
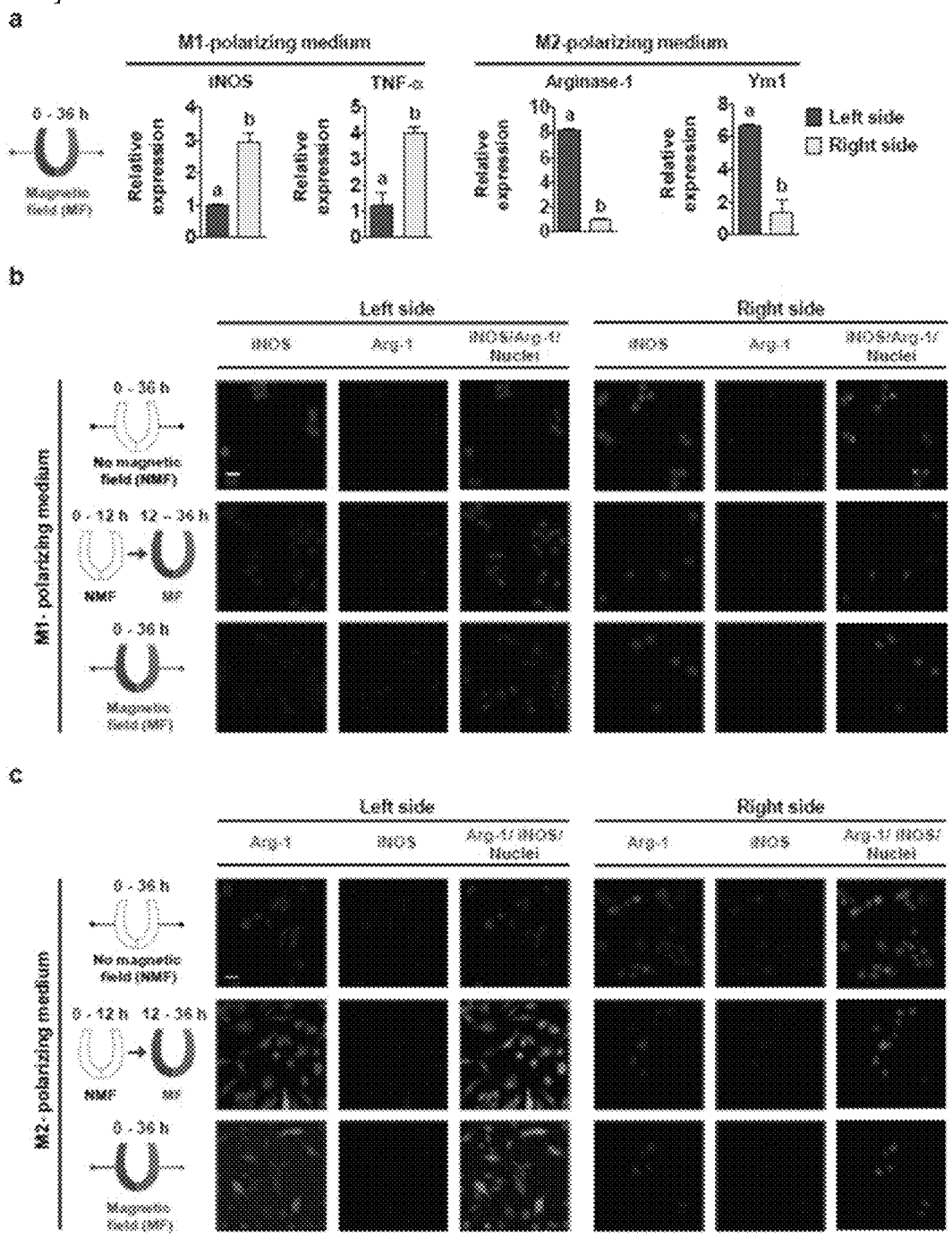

[FIG. 17]
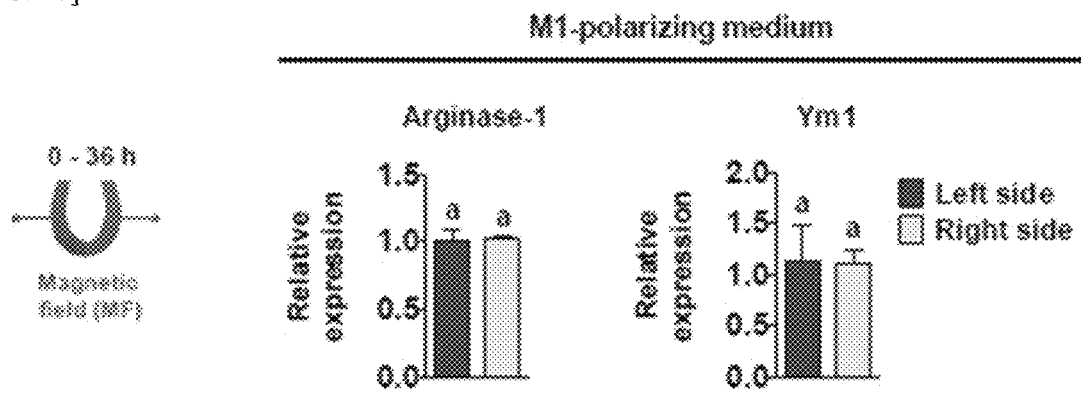
[FIG. 18]
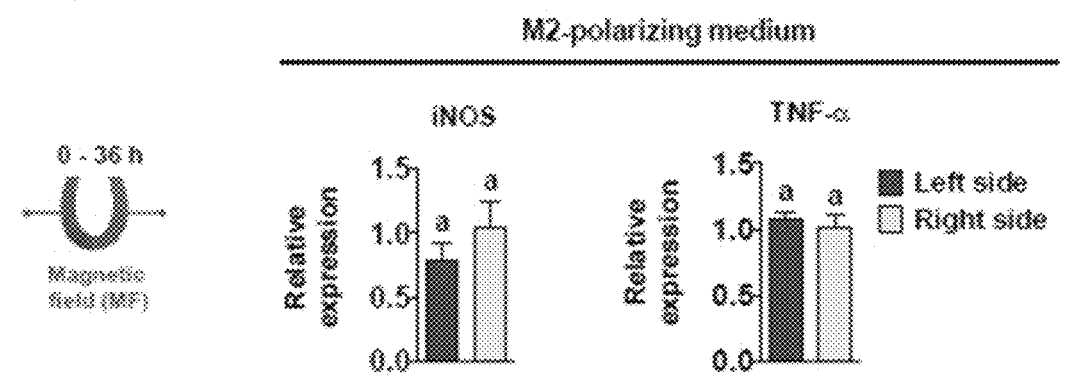
[FIG. 19]
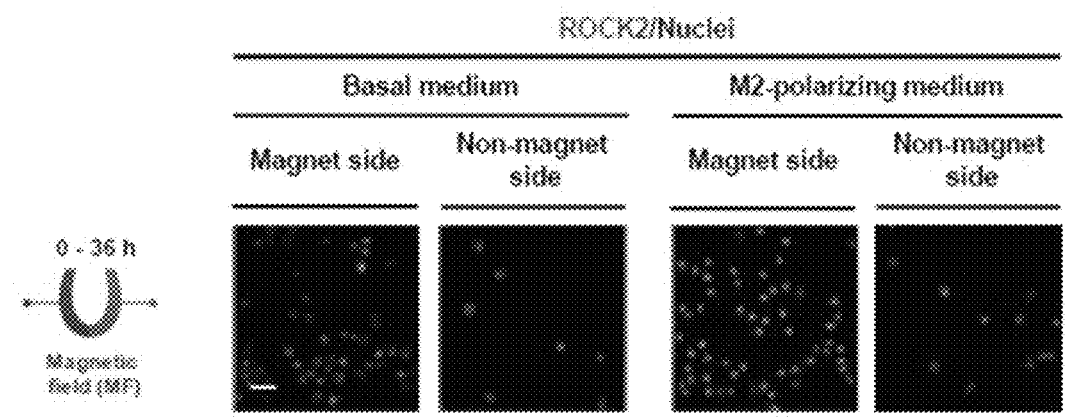

[FIG. 20]
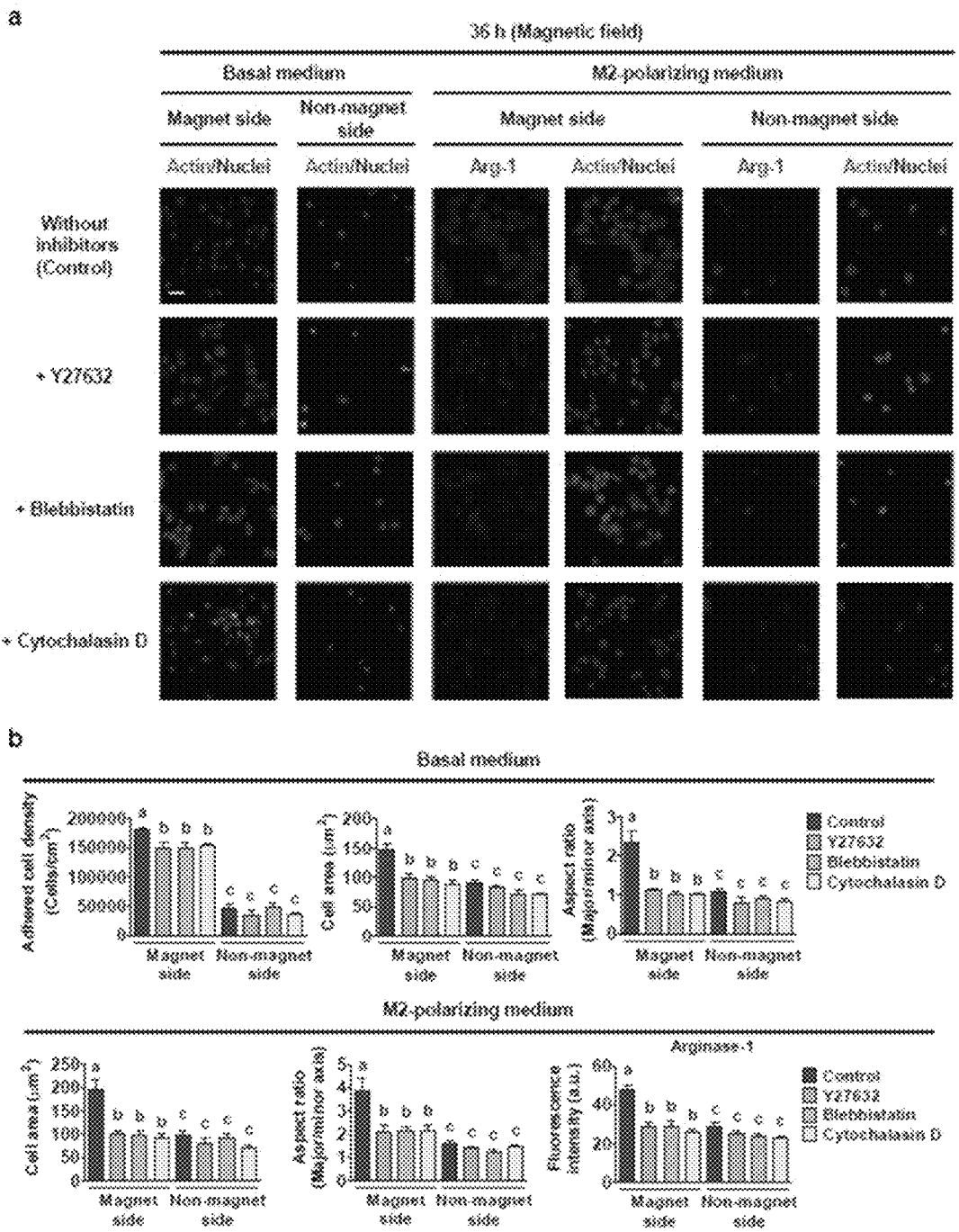

[FIG. 21]
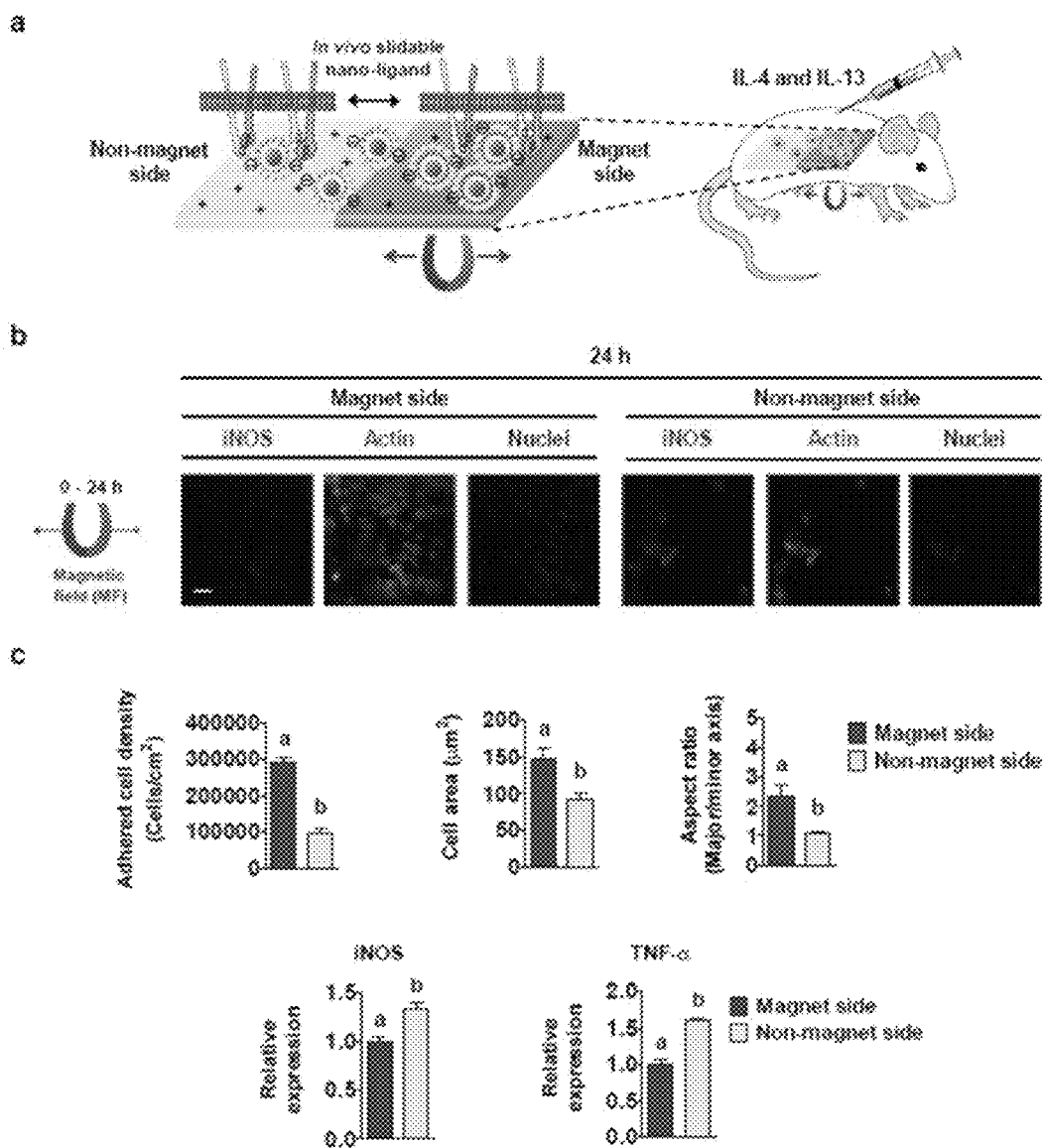

[FIG. 22]
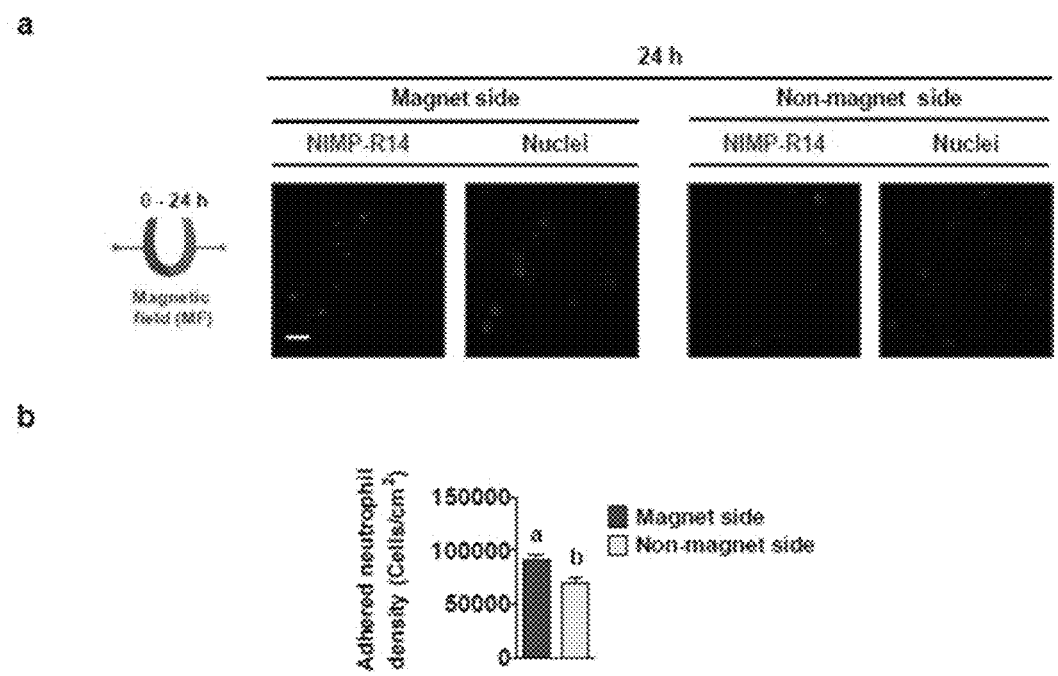

[FIG. 23]
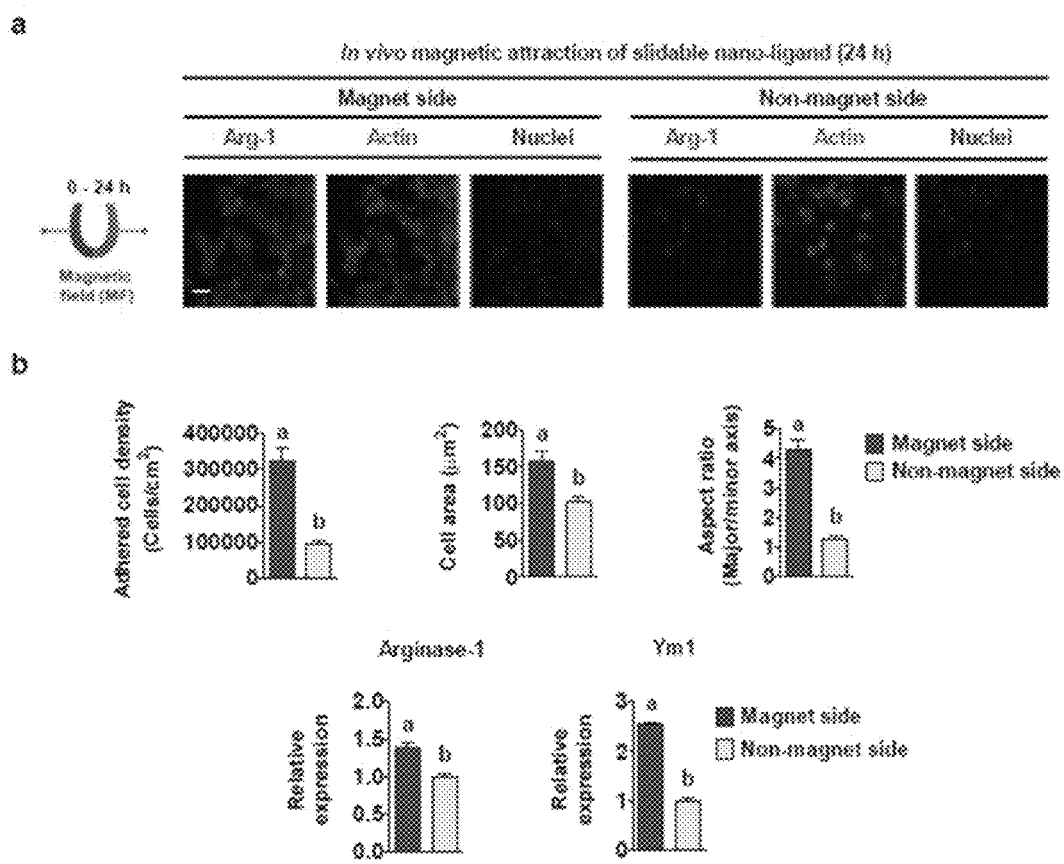

NANO-LIGAND FOR PROMOTING CELL ADHESION AND REGENERATION OF MACROPHAGES AND METHOD OF PROMOTING CELL ADHESION AND REGENERATION OF MACROPHAGES BY USING THE SAME

TECHNICAL FIELD

The present invention relates to a nano-ligand for promoting cell adhesion and regeneration of macrophages and a method of promoting cell adhesion and regeneration of macrophages by using the nano-ligand, and particularly, to a method of remotely controlling cell adhesion and regenerative polarization of macrophages by using the nano-ligand.

BACKGROUND ART

A macrophage is the main cell responsible for innate immunity. Most of the macrophages are fixed in the whole body, but some of the macrophages are present in the form of monocytes in the blood. The monocytes may be divided into dendritic cells or macrophages. Most of the macrophages are fixed, representatively include dust cells, microglial cells, Kupffer cells, and Langerhans cell, and the like, and the macrophages are distributed throughout the body. When antigens invade, the macrophages eat the antigens or secrete toxins to destroy and remove the antigens, and deliver antigens to lymphocytes and trigger an immune response. When an enemy invades the wound, the monocytes in the blood go out of the blood vessels like neutrophils and are divided into macrophages to remove bacteria. Further, the macrophages are divided into a free form which moves to various places in the body and performs phagocytosis, and a fixed form which is fixed to designated organs and performs phagocytosis. The macrophages in the fixed form include liver Kupffer cells, alveolar macrophages, connective tissue structure (histiocyte), and brain microglia cells, and the like.

As a method of efficiently controlling a regenerative effect by M2 polarization and anti-inflammatory effect by M1 polarization of macrophages, a technology through the presentation of ligands in vivo is used. However, the existing presentation of ligands in vivo is mostly static, and even though the presentation of ligands in vivo is dynamic, it is impossible to reversibly change the macroscale nano-ligand density through real-time remote control.

PRIOR ART LITERATURE

Patent Document (Patent Document 1) Korean Patent Application Laid-Open No. 10-2014-0084043

SUMMARY OF THE INVENTION

In order to solve the aforementioned problems, the present invention provides a nano-ligand which is electrostatically coupled with a substrate and is movable, and a method of promoting cell adhesion and regeneration of macrophages by reversibly changing a macroscale ligand density through real-time remote control by using the nano-ligand.

The present invention provides a nano-ligand for promoting cell adhesion and regeneration of macrophages, including: a core including magnetic nano-particles; and a coating layer provided to surround the core and including an integrin-specific ligand peptide, in which the integrin-specific ligand peptide is negatively charged.

Further, the present invention provides a method of preparing the nano-ligand for promoting cell adhesion and regeneration of macrophages, the method including: preparing a core including magnetic nano-particles; preparing a core coupled with a linker by mixing the core and a first suspension including the linker; and mixing the core coupled with the linker and a second suspension including an integrin-specific ligand peptide (RGD).

Further, the present invention provides a method of promoting cell adhesion and regeneration of macrophages, the method including: manufacturing a nano-ligand presenting substrate by putting a substrate, of which a surface is positively charged, in a solution including the nano-ligand for promoting cell adhesion and regeneration of macrophages; and controlling cell adhesion and regenerative polarization of macrophages by treating the nano-ligand presenting substrate with a culture medium and then applying an external magnetic field.

The nano-ligand for promoting cell adhesion and regeneration of macrophages according to the present invention is obtained by coating negatively charged ligands onto a core including magnetic nano-particles, thereby easily moving (sliding) on a substrate through electrostatic bonding with the substrate.

Further, the method of promoting cell adhesion and regeneration of macrophages according to the present invention applies a magnetic field to a substrate including the nano-ligand, so that it is possible to reversibly control the sliding of the nano-ligand as well as temporally and spatially control the sliding of the nano-ligand, and efficiently control cell adhesion and phenotypic polarization of macrophages in vivo or ex vivo through the magnetic field-based spatiotemporal control.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 is a schematic diagram illustrating a nano-ligand for promoting cell adhesion and regeneration of macrophages and a method of promoting cell adhesion and generation of macrophages by using the same according to an exemplary embodiment of the present invention.

FIG. 2 is a diagram illustrating the method of promoting cell adhesion and regeneration of macrophages cells according to the exemplary embodiment of the present invention.

FIG. 3 is a Transmission Electron Micrograph (TEM) image of a slidable nano-ligand according to the exemplary embodiment of the present invention, and in this case, a scale bar indicates 20 nm.

FIG. 4 is a diagram illustrating a characteristic of the slidable nano-ligand according to the exemplary embodiment of the present invention. a of FIG. 4 is a dynamic light scattering image of a magnetic nanoparticles (MNPs) and amino-silica-coated MNPs with size distribution, and b of FIG. 4 is a High-Angle Annular Dark-Field Scanning Transmission Electron Microscopy (HAADF-STEM) image of representative amino-silica-coated MNP, and in this case, a scale bar indicates 20 nm.

FIG. 5 is a Fourier transform infrared spectra image of the slidable nano-ligand according to the exemplary embodiment of the present invention.

FIG. 6 is a vibrating sample magnetometer hysteresis of the slidable nano-ligand according to the exemplary embodiment of the present invention.

FIG. 7 is a diagram illustrating electrostatic coupling of the slidable nano-ligand to a substrate according to the exemplary embodiment of the present invention.

FIG. 8 is an image photographed by Scanning Electron Microscopy (SEM) and Atomic Force Microscopy (AFM) of in situ reversible spatiotemporal manipulation of both macroscale and nanoscale nano-ligand sliding according to the exemplary embodiment of the present invention. a and b of FIG. 8 are images of a positively charged substrate and a nano-ligand, c and d of FIG. 8 are results of time-lapse SEM imaging, and e of FIG. 8 represents nanoscale displacement of nano-ligand sliding through AFM scanning.

FIG. 9 is an AFM image of in situ nano-ligand sliding in the absence of a permanent magnet of a Comparative Example.

FIG. 10 is a diagram illustrating modulation of integrin β1 binding of in situ control of a sliding nano-ligand according to the exemplary embodiment of the present invention. a of FIG. 10 is a schematic diagram of a sliding nano-ligand with a permanent magnet positioned under the "left" side of the substrate, b of FIG. 10 is an immunofluorescent confocal microscope image of integrin β1 clusters bound to the slidable nano-ligand at the "left", "middle", and "non-magnet" sides of the substrate, and in this case, a scale bar indicates 50 μm, and c of FIG. 10 is a graph illustrating quantification of staining intensity of integrin 131 clusters at the "magnet", "middle", and "non-magnet" sides of the substrate.

FIG. 11 is an image representing a result of the in situ control experiment of the nano-ligand sliding according to the exemplary embodiment of the present invention. a of FIG. 11 is a schematic images of manipulating the slidable nano-ligand by positioning a permanent magnet at the bottom of the substrate ("magnet" side) with corresponding confocal microscope images of immunofluorescent staining against vinculin, actin, and nuclei after 24 hours of culturing macrophages subjected to a magnet placed at the bottom of the substrate ("magnet" side). b of FIG. 11 is a graph illustrating quantification of the macrophage density, cell area, and cell aspect ratio.

FIG. 12 is a diagram illustrating a result of an adhesion experiment of macrophages according to a comparative example. a of FIG. 12 is a confocal microscope image of immunofluorescent staining of the macrophages for vinculin, F-actin, and nuclei after culturing the macrophages for 24 hours in the absence of an RGD peptide ligand or a magnetic field. b of FIG. 12 is a graph illustrating quantification of macrophage density, area, and aspect ratio.

FIG. 13 is a diagram illustrating a result of an experiment of controlling adhesion of macrophages through the control of the macroscale nano-ligand according to the exemplary embodiment of the present invention. a of FIG. 13 is an immunofluorescent confocal microscope image against vinculin with F-actin and nuclei after 12 hours or 24 hours of culturing macrophages subjected to placing a permanent magnet at the bottom of the substrate ["magnetic field (MF)"] or withdrawing the permanent magnet from the substrate ["no magnetic field (NMF)"]. b of FIG. 13 is a graph of a calculation of the macrophage density, cell area, and cell aspect ratio for the "left" side of the substrate.

FIG. 14 is a graph illustrating quantification of macrophage density, cell area, and aspect ratio for the "right" surface of the substrate according to time regulation of the nano-ligand according to the exemplary embodiment of the present invention.

FIG. 15 is a confocal microscope image of immunofluorescence for temporal conversion of macroscale nano-ligand presentation according to the exemplary embodiment of the present invention, and b of FIG. 15 is a graph illustrating a calculation of macrophage density, cell area, and cell aspect ratio.

FIG. 16 is a diagram illustrating a result of a phenotype experiment according to time-regulated magnetic attraction of the nano-ligand according to the exemplary embodiment of the present invention. a of FIG. 16 is a graph illustrating quantitative gene expression of M2 phenotype markers (Arginase-1 and Ym1) for macrophages cultured under M2-polarizating medium or M1 phenotype markers (iNOS and TNF-α) for macrophages cultured under M1-polarizating medium. b and c of FIG. 13 are confocal microscope images of immunofluorescence against iNOS with Arg-1 and nuclei of cultured macrophages.

FIG. 17 is a graph illustrating M2 phenotype of macrophages in the M1 polarizing medium of the slidable nano-ligand according to the exemplary embodiment of the present invention.

FIG. 18 is a graph illustrating M1 phenotype of macrophages in the M2 polarizing medium of the slidable nano-ligand according to the exemplary embodiment of the present invention.

FIG. 19 is a confocal microscope image of immunofluorescence of an M2 phenotype experiment of macrophages for magnetic attraction of the slidable nano-ligand according to the exemplary embodiment of the present invention.

FIG. 20 is a confocal microscope image of immunofluorescence (a) of a magnetic attraction regulating experiment of the nano-ligand according to the exemplary embodiment of the present invention, and b of FIG. 20 is a graph illustrating calculation of the density, cell area, and cell aspect ratio of the adherent macrophages or the area, aspect ratio, and Arg-1 staining intensity after culturing in M2 medium.

FIG. 21 is a diagram illustrating an experiment of adherent and inflammatory M1 phenotype of host macrophages in vivo against magnetic attraction of the slidable nano-ligand according to the exemplary embodiment of the present invention. a of FIG. 21 is a schematic diagram of magnetic control of the slidable nano-ligand in vivo. b of FIG. 21 is a confocal microscope image of immunofluorescence against iNOS, F-actin, and nuclei of cells adhered to the "magnet" and "non-magnet" sides of the substrate. c of FIG. 21 is a graph illustrating calculation of the density, cell area, and cell aspect ratio (n=30) as well as gene expression profiles (n=3) of M1 phenotype markers (iNOS and TNF-α) of the in vivo adhered cells.

FIG. 22 is a diagram illustrating a result of an experiment of in vivo adhesion of host neutrophils for the slidable nano-ligand according to the exemplary embodiment of the present invention. a of FIG. 22 is a confocal microscope images of immunofluorescent staining against NIMP-R14, F-actin, and nuclei of host cells adhered to the "magnet" and "non-magnet" sides of the substrate presenting the slidable nano-ligand after 24 hours of subcutaneous implantation with an injection of IL-4 and IL-13 onto the substrate. b of FIG. 22 is a graph illustrating quantification of the density of the in vivo adhered NIMP-R14-positive host neutrophils.

FIG. 23 is a diagram illustrating a result of an experiment of adherent and regenerative M2 phenotype of host macrophages in vivo for magnetic attraction of the slidable nano-ligand according to the exemplary embodiment of the present invention. a of FIG. 23 is a confocal microscope image of immunofluorescence against Arg-1, F-actin, and nuclei of cells adhered to the "magnet" and "non-magnet" sides of the substrate presenting the slidable nano-ligand after 24 hours of subcutaneous implantation with an injection of IL-4 and IL-13 onto the substrate. b of FIG. 23 is a graph illustrating calculation of the density, cell area, and cell aspect ratio (n=30) as well as gene expression profiles (n=3) of M2 phenotype markers (Arg-1 and Ym1) of the in vivo adhered cells.

DETAILED DESCRIPTION

Hereinafter, in order to describe the present invention in more specifically, an exemplary embodiment of the present invention will be described in more detail with reference to the accompanying drawings. However, the present invention is not limited to the exemplary embodiment described herein, and may also be specified in other forms.

Macrophages dynamically interact with the continuously remodeled extracellular matrix (ECM), thereby giving rise to spatially and temporally disparate macroscale ligand distribution in vivo. A nano-ligand for promoting cell adhesion and regeneration of macrophages according to the present invention allows the reversible remote control by spatially and temporally varying the macroscale nano-ligand distribution, so that it is possible to emulate ECM remodeling and regulate the adhesion and polarization of macrophages to spatially and temporally control host responses. In the nano-ligand of the present invention, the negatively charged sliding nano-ligand is coupled with a positively charged substrate through electrostatic interaction, and the slidability of nano-ligand was optimized by utilizing magnetic core nanoparticles that were coated with polymer linker and negatively charged RGD ligand. The present characterized the macroscale and in situ nanoscale nano-ligand sliding under an external magnetic field, which spatiotemporally and reversibly altered the macroscale nano-ligand density. Further, the present invention presents unprecedented in situ manipulation of the macroscale ligand density by magnetically attracting the slidable nano-ligand to regulate the adhesion and polarization phenotypes of host macrophages in vivo. Specifically, the time-regulated magnetic attraction of the slidable nano-ligand inhibited inflammatory M1 phenotype of macrophages but stimulated regenerative M2 phenotype. Furthermore, the magnetic attraction of the slidable nano-ligand of the present invention facilitates the assembly of adhesion structures in macrophages, thereby stimulating polarization of the macrophages to the M2 phenotype. Therefore, the nano-ligand of the present invention enables the spatiotemporal regulation of immunomodulatory tissue-regenerative responses to implants in vivo through remote, spatiotemporal, and reversible controllability of the macroscale ligand density.

The present invention provides a nano-ligand for promoting cell adhesion and regeneration of macrophages, including: a core including magnetic nanoparticles; and a coating layer provided so as to surround the core and including an integrin-specific ligand peptide, in which the integrin-specific ligand peptide is negatively charged.

FIG. 1 is a schematic diagram illustrating a nano-ligand for promoting cell adhesion and regeneration of macrophages and a method of promoting cell adhesion and generation of macrophages by using the same according to an exemplary embodiment of the present invention.

Referring to FIG. 1, it can be seen that the nano-ligand of the present invention includes: a core including magnetic nanoparticles; and a coating layer coupled to a core and including an integrin-specific ligand peptide, in which the integrin-specific ligand peptide is a negatively charged integrin-specific peptide. In particular, the integrin-specific ligand peptide coupled to the core may have the form surrounding the core, like a micelle structure. Accordingly, a surface charge of the nano-ligand may represent a negative charge. For example, a superparamagnetic core iron oxide nanoparticle in the slidable nano-ligand is first synthesized, the superparamagnetic core nanoparticle is functionalized with functional amino-silica shell, and then coated with a polyethylene glycol (PEG) linker to enhance the slidability of nano-ligand to which a negatively charged RGD peptide ligand (CDDRGD) is grafted.

Further, FIG. 3 is a Transmission Electron Micrograph (TEM) image of the nano-ligand for promoting cell adhesion and regeneration of macrophages according to the present invention, and a size of the nano-ligand can be recognized. In particular, the nano-ligand may have a diameter of 30 to 60 nm. When the diameter of the nano-ligand is less than 30 nm, it is difficult to control a movement of the nano-ligand, and when the diameter of the nano-ligand is larger than 60 nm, cell adhesion efficiency of the macrophages may be degraded. In more particular, the nanobarcode may have a diameter of 30 nm to 50 nm, or 35 nm to 45 nm.

As long as the magnetic nanoparticles are nanoparticles having magnetic properties, the magnetic nanoparticles are not particularly limited. For example, the magnetic nanoparticles may have a diameter of 5 to 30 nm. When the diameter of the nanoparticle is less than 5 nm, the particle is too small, resulting in large loss and reducing efficiency, and when the diameter of the nanoparticle is larger than 30 nm, the diameter of the nano-ligand increases, resulting in degrading cell adhesion efficiency of macrophages. More particularly, the magnetic nanoparticle may have a diameter of 5 nm to 15 nm, or 10 nm to 20 nm. The nano-ligand includes the magnetic nanoparticles as described above, so that the nano-ligand of the present invention may promote cell adhesion and regeneration of macrophages by using a magnetic field.

Further, in the magnetic nanoparticle, silica may be coated to a surface. In particular, in the magnetic nanoparticle, amino-silica may be coated to the surface. The kind of the silica may be any one or more of tetraethyl orthosilicate (TEOS) and (3-Aminopropyl)triethoxysilane (APTES).

For example, the nano-ligand of the present invention has a structure in which the core and the coating layer are connected by the linker, and the linker may be a polyethylene glycol (PEG)-based linker. In particular, the polyethylene glycol (PEG) linker may be maleimide-poly(ethylene glycol)-NHS ester (Mal-PEG-NHS ester). The present invention includes the linker, thereby improving coupling force between the core and the coating layer and improving durability of the nano-ligand.

The coating layer is coupled to the core or the linker coupled with the core, and has the form surrounding the core. In particular, the coating layer includes the integrin-specific ligand peptide (RGD), and the integrin-specific ligand peptide may have the negatively charged form and include a negatively charged thiolated integrin-specific ligand peptide. The present invention includes the negatively charged thiolated integrin-specific ligand peptide, so that the surface of the nano-ligand of the present invention has the negatively charged form, and accordingly, the nano-ligand may freely move on a substrate through the electrostatic coupling with the substrate. By the characteristic, the nano-ligand is also referred to as the "slidable nano-ligand", and may promote cell adhesion and regeneration of macrophages through sliding of the nano-ligand on the substrate.

Further, the present invention provides a method of preparing the nano-ligand for promoting cell adhesion and regeneration of macrophages, the method including: preparing a core including magnetic nanoparticles; preparing a core coupled with a linker by mixing the core and a first suspension including the linker; and mixing the core coupled with the linker and a second suspension including an integrin-specific ligand peptide (RGD).

The preparing of the core may include forming the silane-coated core by stirring the magnetic nanoparticles with a silane solution. In particular, the preparing of the core may include forming an amino-silane coated core by stirring the magnetic nanoparticles with an amino-silane solution. The kind of the silane included in the silane solution may be any one or more of tetraethyl orthosilicate (TEOS) and (3-Aminopropyl)triethoxysilane (APTES).

In particular, the preparing of the core coupled with the linker may be performed by stirring the core in a suspension including the linker for 10 to 20 hours or 10 to 15 hours under the dark condition. Accordingly, the linker-coupled core may be obtained. In this case, the linker-coupled core may be obtained by washing the core mixed with the suspension with a solvent two or more times by using the permanent magnet. The solvent may contain any one or more of dimethylformaldehyde (DMF) and dimethyl sulfoxide (DMSO).

In this case, the linker may be a polyethylene glycol (PEG) linker. In particular, the polyethylene glycol (PEG) linker may be maleimide-poly(ethylene glycol)-NHS ester (Mal-PEG-NHS ester). By coupling the linker to the core, it is possible to improve coupling force between the core and the coating layer and improve durability of the nano-ligand.

Further, the mixing of the core with the second suspension may be performed by stirring the core coupled with the linker in a suspension including the integrin-specific ligand peptide (RGD) for 10 to 20 hours or 10 to 15 hours under the dark condition. In this case, the magnetic nanoparticles (nano-ligands) coupled with the negatively charged integrin-specific ligand peptide may be obtained by using the solvent using the permanent magnet. The solvent may contain any one or more of dimethylformaldehyde (DMF) and dimethyl sulfoxide (DMSO).

Herein, the coating layer may be formed on the core through the process of stirring the integrin-specific ligand peptide. In particular, the integrin-specific ligand peptide may be the negatively charged form, and may be the negatively charged thiolated integrin-specific ligand peptide. The coating layer is formed on the core with the negatively charged integrin-specific ligand peptide, so that the surface of the nano-ligand of the present invention may have the negatively charged form, resulting in the free movement of the nano-ligand on the substrate through the electrostatic coupling with the substrate. By the characteristic, the nano-ligand is also referred to as the "slidable nano-ligand", and may promote cell adhesion and regeneration of macrophages through sliding of the nano-ligand on the substrate.

Further, the present invention provides a method of promoting cell adhesion and regeneration of macrophages, including: manufacturing a nano-ligand presenting substrate by putting a substrate, of which a surface is positively charged, in a solution including the nano-ligand for promoting cell adhesion and regeneration of macrophages; and controlling cell adhesion and regenerative polarization of macrophages by treating the nano-ligand presenting substrate with a culture medium and then applying an external magnetic field.

FIGS. 1 and 2 are diagrams illustrating the method of promoting cell adhesion and regeneration of macrophages according to the exemplary embodiment of the present invention. Referring to FIGS. 1 and 2, it can be seen that the nano-ligand, of which the surface is negatively charged, is electrostatically coupled onto the positively charged substrate, following by applying a magnetic field, so that cell adhesion of macrophages is promoted, inflammatory M1 phenotype is inhibited, and regenerative M2 phenotype is activated in the part to which the magnetic field is applied. In particular, the substrate and the nano-ligand are coupled through the electrostatic coupling, so that the nano-ligand moves (slides) along the location to which the magnetic field is applied, and thus it is possible to promote cell adhesion and regeneration of macrophages in a desired region by regulating a density of the nano-ligand in the portion to which the magnetic field is applied.

In particular, the manufacturing of the nano-ligand presenting substrate includes: soaking the surface of the substrate in an acid solution; activating the surface of the substrate so that the surface of the substrate is positively charged by putting the soaking-completed substrate in an amino-silane solution; and treating the substrate, of which the surface is positively charged, by using ultrasonic waves at a room temperature.

The soaking of the surface of the substrate in the acid solution may include soaking the surface of the substrate in an acid solution containing any one or more of hydrochloric acid and sulfuric acid for 30 minutes to 2 hours or 30 minutes to 1 hour. Through this, bonding with an amino group is facilitated by bonding a hydroxyl group to the surface of the substrate, thereby effectively performing activation of the surface of the substrate.

The activating of the surface of the substrate may include activating the surface of the substrate so that the surface of the substrate exhibits positive charges by putting the substrate in the amino-silane solution under the dark condition. The amino-silane solution may include (3-aminopropyl) triephoxysilane (APTES). In this case, the activation of the surface of the substrate means that the surface of the substrate is positively charged, and particularly, the surface of the substrate may be activated by binding an amine group onto the substrate. The surface of the substrate is positively charged by activating the surface of the substrate by soaking the substrate in the amino-silane solution, so that the substrate may be coupled with the nano-ligand by electrostatic attraction.

Further, the treating of the substrate, of which the surface is positively charged, by using ultrasonic waves may include manufacturing the nano-ligand presenting substrate by putting the substrate, of which the surface is positively charged, in the solution including the nano-ligand. In particular, the treating of the activated substrate by using ultrasonic waves was performed by putting the substrate, of which the surface is positively charged, in the solution including the nano-ligand under ultrasonic-wave treatment in purified water for 30 minutes to 2 hours or 30 minutes to 1 hour at a room temperature.

The controlling the cell adhesion and regenerative polarization of macrophages may be performed by positioning the nano-ligand presenting substrate in vivo or ex vivo and then applying a magnetic field of 100 to 700 mT for 12 to 48 hours. In particular, the controlling the cell adhesion and regenerative polarization of macrophages may be performed by locating the nano-ligand presenting substrate in vivo or ex vivo and then applying a magnetic field of 100 to 600 mT, 200 to 600 mT, or 300 to 550 mT for 12 to 36 hours, 24 to 26 hours, or 12 to 24 hours. By applying the magnetic field to the nano-ligand presenting substrate, it is possible to promote cell adhesion of macrophages to the nano-ligand located on the substrate, and also inhibit polarization of the inflammatory M1 phenotype of the adhered macrophages and promote polarization of the regenerative M2 phenotype.

Further, the controlling of the cell adhesion and regenerative polarization of macrophages may be performed by changing the location in the substrate to which the magnetic field is applied. In particular, the cell adhesion and regenerative polarization of macrophages may be spatially controlled by changing the location in the substrate, to which the magnetic field is applied, while applying the magnetic field of 100 to 600 mT, 200 to 600 mT, or 300 to 550 mT. For example, it is possible to promote the cell adhesion and regeneration of macrophages only in a desired portion of the substrate by regulating the density of nano-ligands on the substrate by applying the magnetic field to a part of the substrate, and inhibit polarization of the inflammatory M1 phenotype of the adhered macrophages and promote polarization of the regenerative M2 phenotype.

In addition, the controlling the cell adhesion and regeneration of macrophages may be performed by changing the location of the magnetic field applied to a lower end of the substrate over time. In particular, the cell adhesion and phenotype of the macrophages may be temporally and spatially controlled by changing the location in the substrate to which the magnetic field is applied while applying the magnetic field of 100 to 600 mT, 200 to 600 mT, or 300 to 550 mT. More particular, it is possible to control the degree of promotion of the cell adhesion and regenerative M2 polarization of the macrophages in each portion on the substrate by regulating the density of the nano-ligands located on the substrate over time by individually applying the magnetic field to each portion of the substrate. For example, in the case where the magnetic field is applied to the left side of the substrate for 12 to 24 hours and the magnetic field is applied to the right side of the substrate for 24 to 36 hours, the amount of macrophages adhered to the left side and the right side of the substrate or the macrophages of the regenerative M2 polarization may be varied Hereinafter, examples of the present invention will be described. However, the examples below are merely preferable examples of the present invention, and the scope of the present invention is not limited by the examples.

Preparation Example

Preparation Example 1

Prepare Slidable Nano-Ligand
1) Prepare Magnetic Core (MNP)
For the magnetic control of a slidable nano-ligand, a magnetic core of a slidable nano-ligand was prepared as described below. About 80 mL of ethanol, 60 mL of deionized (DI) water, and 140 mL of heptane were first mixed. To this mixture, 120 mmol of sodium oleate and 40 mmol of iron (III) chloride hexahydrate were added to a solvent mixture of 80 ml of ethanol, 60 mL of deionized (DI) water, and 140 mL of heptane at 70° C. for 4 hours under an inert environment.
The heptane layer including an iron-oleate was collected and washed with DI water. The heptane was then evaporated off to collect the dried iron oleate, to which 20 mmol of oleic acid and 200 g of 1-octadecene were added to approximately 40 mmol of the dried iron-oleate. This solution was stirred at 100° C. for approximately 5 minutes. The temperature was then raised to 320° C. and maintained for approximately 30 minutes. The mixture solution was suspended under air, allowed to be cool to room temperature and then washed with ethanol three times using a permanent magnet to collect the nanoparticle. In order to store this magnetic core nanoparticle (MNP), the solution was stored in heptane until used.

2) Functionalization of Amino-Silica of Magnetic Core (Amino-Silica Coated MNP)

The magnetic core nanoparticle was coated with an amino-silica shell for the nanoassembly of slidable nano-ligand. The magnetic core nanoparticle (30 mg) was dispersed in cyclohexane (25 mL). To this suspension, triton-X (5 mL), 1-hexanol (5 mL), ammonium hydroxide (0.5 mL), and DI water (1 mL) were serially added, which was stirred for 30 minutes. After stabilizing the emulsion, tetraethyl orthosilicate (TEOS, 12.5 µL) was slowly mixed and stirred for 10 minutes. For amino-functionalization, (3-aminopropyl)triethoxysilane (APTES, 6.25 µL) was mixed and stirred overnight. Following amino-functionalization, the amino-silica shell coated MNP was washed with acetone and dimethylformamide (DMF), three times each, which was collected with a magnet.

3) Prepare Slidable Nano-Ligand the sliding property of nano-ligand was enhanced by using a polyethylene glycol (PEG) linker, and then the negatively charged RGD peptide ligands were grafted onto the surface amino-silica shell coated MNP. The PEG linker was used in the nanoassembly of the slidable nano-ligand to prevent cellular uptake. Amino-silica shell coated MNP in DMF (1 mL) was used to dissolve 5 mg of Maleimide-poly (ethylene glycol)-NHS ester (Molecular weight: 5 kDa, Biochempeg). N,N-Diisopropylethylamine (DIPEA, 2 µl) was added to this suspension and stirred overnight in the dark, which was subsequently washed with DMF three times and dimethyl sulfoxide (DMSO) three times, after which it was collected using a permanent magnet. The PEG-amino-silica shell coated MNP in DMSO (1 mL) was added to dissolve the negatively charged thiolated RGD peptides (CDDRGD, GL Biochem, 0.5 mg). DIPEA (2 µl) and tris(2-carboxyethyl)phosphine hydrochloride (TCEP, 10 mM) were added to this suspension to avoid the formation of disulfide bonds and the mixture was stirred overnight in the dark. The suspension was washed with DMSO and the slidable nano-ligand was collected by using a permanent magnet prior to coupling with the substrate that is coupled via electrostatic interaction.

Comparative Preparation Example 1

A "No RGD" nano-ligand was prepared by the same method as that of Preparation Example 1 except that a negatively charged thiolated RGD peptide (CDDRGD, GL Biochem) was not added.

EXAMPLE

Example 1

Slidable Nano-Ligand and Coupling of Slidable Nano-Ligand with Substrate
In order to reversibly couple the slidable nano-ligand prepared in the Preparation Example to the substrate, culture-grade glass coverslips (22 mm×22 mm) were used. The substrates were soaked in the 1:1 mixture of hydrochloric acid and methanol for 30 minutes to remove any organic impurities and then washed with DI water. The substrate was soaked in sulfuric acid for one hour and washed with deionized water. The substrates were subjected to the soaking in 1:1 mixture of 3-aminopropyltriethoxysilane (APTES) and ethanol for 1 hour in the dark condition to achieve the amination of the substrates. The substrates were then washed with ethanol and dried at 100° C. for 1 hour. To facilitate the electrostatic interactions, the negatively charged slidable nano-ligand (RGD-PEG-amino silica shell-coated magnetic nanoparticles) in 1 mL of DMSO was diluted with DMSO (1:20) and then incubated with the positively charged aminated substrates for 1 hour under the sonication. The substrates were washed with DI water to yield the slidable nano-ligand existing substrates.

Experimental Example

Experimental Example 1

In order to check the form of the slidable nano-ligand according to the present invention, Transmission Electron Micrograph (TEM), dynamic light scattering, and High-Angle Annular Dark-Field Scanning TEM (HAADF-STEM) analysis were performed on the slidable nano-ligand, and the result of the analysis is represented in FIGS. 3 and 4.

Further, in order to check the property and a chemical bonding characteristic of the slidable nano-ligand, Vibrating-Sample Magnetometry and Fourier Transform Infrared Spectroscopy (FTIR) were performed on the slidable nano-ligand, and the result thereof is represented in FIGS. 5 and 6.

In particular, in the TEM experimental, TEM imaging was performed by using Tecnai 20 (FEI, USA) in order to check a size and a shape characteristic of the slidable nano-ligand.

Further, High-Angle Annular Dark-Field Scanning Transmission Electron Microscopy (HAADF-STEM) is to characterize the size and shape characteristic of the representative slidable nano-ligand, and HAADF-STEM imaging was carried out by using JEOL 2100F with 1 nm probe size, 20 μm condenser aperture, and 80 to 150 mrad collection angle for Z contrast.

In addition, in Dynamic Light Scattering (DLS) analysis, in order to quantify the size distribution profile (hydrodynamic diameter) in the assembly process of sliding nano-ligand, DLS measurement (Zetasizer Nano ZS90 Malvern Panalytical, Malvern, UK) was carried out.

Further, the FT-IR was carried out by using GX1 (Perkin Elmer Spectrum, USA) in order to confirm the serial chemical changes in the modification of slidable nano-ligand. The samples subjected to the analysis of changes in chemical bond characteristics were lyophilized and densely packed into KBr pellet prior to the analysis.

In order to characterize the reversible slidable (superparamagnetic) property of the nano-ligand, the magnetic nanoparticle core in the slidable nano-ligand was subjected to the VSM measurement (EV9; Microsense) at a room temperature under the applied magnetic field. The corresponding magnetic moment was presented in a hysteresis loop after normalization to the dry weight with the magnetic core in the slidable nano-ligand.

FIG. 3 is a Transmission electron micrograph (TEM) image of a nanoscale image of the slidable nano-ligand and in this case, a scale bar indicates 20 nm. a of FIG. 4 is a result of dynamic light scattering of magnetic nanoparticles (MNPs) and amino-silica-coated MNPs with size distribution, and b of FIG. 4 is an HAADF-STEM image of the amino-silica-coated MNP, and in this case, a scale bar indicates 20 nm.

Referring to FIG. 3, the slidable nano-ligand was visualized by transmission electron micrograph (TEM), which revealed uniform morphology of sphere of the slidable nano-ligand including a superparamagnetic core (16±2 nm) and a slidable nano-ligand core-shell (42±5 nm). Further, referring to FIG. 4, as determined by dynamic light scattering, the uniform diameter of the superparamagnetic core of 15±4 nm and slidable nano-ligand core-shell of 41±5 nm, which was consistent with TEM and high-angle annular dark-field scanning TEM (HAADF-STEM) images.

FIG. 5 is a Fourier transform infrared spectra image of the slidable nano-ligand according to the exemplary embodiment of the present invention. In particular, FIG. 5 is the Fourier transform infrared spectra image of the MNP, the silica-coated MNP, and the RGD ligand-presenting PEG grafted silica-coated MNP (RGD-PEG-silica-coated MNP, slidable nano-ligand). FIG. 6 is a vibrating sample magnetometer hysteresis of the slidable nano-ligand.

Referring to FIG. 5, the change in the chemical bonding in the process of preparing the slidable nano-ligand can be recognized through the FTIR. In particular, Fe—O binding was detected at the absorption peak value of 699 $cm^{-1}$ in superparamagnetic iron oxide core nanoparticles. Si—O binding was detected at the absorption peak value of 1168 $cm^{-1}$ in the silica shell. In the slidable nano-ligand, the PEG linker ($M_n$=5,000 Da) improve the sliding property and inhibits uptake by cells as demonstrated in previous literature, and CDDRGD represented C=O bonding at the absorption peak of 1152 $cm^{-1}$ and amide bonding at the absorption peak of 1635 $cm^{-1}$. The FTIR analysis confirmed the successful assembly of the slidable nano-ligand.

Referring to FIG. 6, the result of the analysis confirmed the superparamagnetic property of 20 emu/g Ms. Through this, the slidable nano-ligand according to the present invention exhibits the superparamagnetic property to be reversibly slidable, so that the superparamagnetic property is very important to magnetically manipulating the sliding of the nano-ligand temporally and reversibly.

Experimental Example 2

In order to verify in situ reversible spatiotemporal control of the slidable nano-ligand according to the present invention, the slidable nano-ligand was photographed with the SEM, and AFM imaging was carried out, and the result thereof is represented in FIGS. 8 and 9.

FIG. 7 is a diagram illustrating electrostatic coupling of the slidable nano-ligand to a substrate according to the exemplary embodiment of the present invention. Referring to FIG. 7, magnetic nanoparticles (core) were PEGylated and subsequently coated with negatively charged RGD peptide ligand (CDDRGD) to form slidable nano-ligand, which was coupled to the positively charged substrate via an electrostatic interaction. In particular, as illustrated in FIG. 7, In particular, as illustrated in FIG. 7, in order to electrostatically control the macroscale nano-ligand presentation, in the present invention, the slidable ligand was coupled to the positively charged substrate for in situ spatiotemporally controlling the sliding of the nano-ligand. Through the electrostatic coupling of the nano-ligand and the substrate, reversible movement of the sliding of the nano-ligand was allowed.

Herein, the SEM is for the purpose of confirming the negatively charged slidable nano-ligand coupled to the positively charged substrate via an electrostatic interaction, and Field emission-SEM imaging (FE-SEM, FEI, Quanta 250 FEG) was conducted on the dried and platinum-coated substrate. The density of the substrate-conjugated slidable nano-ligand was determined with Image J using 10 different images. SEM imaging was also conducted to characterize reversible and spatiotemporal manipulation of macroscale ligand density. The position of a permanent magnet (150 mT) was switched from the bottom left side of the substrate to the bottom right side, and then to the bottom left side back again every 12 hours. The corresponding changes in the macroscale ligand density were calculated using Image J, and the result of the calculation is represented in FIG. 8.

Further, in order to confirm the characteristics of in situ 2 and 3D images of slidable nano-ligand on the substrate, in situ magnetic Atomic Force Microscopy (AFM) imaging (Asylum Research, XE-100 System) was carried out in AC in air mode at 25° C. The imaging was carried out in AC by using AFM cantilever (Nanosensors, SSS-SEIHR-20) with a spring constant of 5-3 N/m and a resonance frequency of 96-175 kHz. For static serial imaging in the absence of a magnet near the substrate, the imaging was conducted on the same scanning area of the substrate to examine the non-magnet-mediated displacement of the slidable nano-ligand. For in situ magnetic imaging, the imaging was first conducted and then a permanent magnet was placed at the bottom of the substrate but at the opposite side of the scanning area, and subsequently, the imaging was conducted in the same scanning area for characterizing in situ nanoscale nano-ligand sliding.

FIG. 8 is an image for in situ reversible spatiotemporal manipulation of sliding of macroscale and nanoscale nano-ligands. Referring to a and b of FIG. 8, the positively charged amino-functionalized substrate was optimally and homogeneously coupled with the nano-ligand as evidenced by the SEM and the 3D AFM. Further, the macroscale density of the nano-ligand was calculated as 20±3 nano-ligand particles/µm². It can be seen that this density was optimal for the effective control of slildability of the nano-ligand, which did not cause the aggregation of the slidable nano-ligand. Accordingly, the nano-ligand of the present invention is reversibly slidable (movable) on the substrate, so that it is possible to spatiotemporally and reversibly control cell adhesion and phenotype of the macrophages.

c and d of FIG. 8 are SEM imaging results of the spatiotemporal control experiment, and it can be seen that it is possible to control slidability by regulating the density of the macroscale nano-ligand by using the magnetic control. In particular, in the SEM imaging, a permanent magnet was positioned under the left side of the substrate to attract the slidable nano-ligand toward the left side, switched to the right side, and reverted to the left side each 12 hours. In the time-lapse SEM imaging, compared to the right side, the nano-ligand density on the left side was significantly higher by 81% after 12 hours, lower by 31% after 24 hours, but higher by 82% after 36 hours.

e of FIG. 8 is a comparative example of the spatiotemporal control experiment, and shows nanoscale displacement of nano-ligand sliding through serial in situ magnetic AFM scanning on the identical area regardless of the existence of an external magnetic field in the scanning area. In e of FIG. 8, the magnetic field was generated by placing a magnet at the bottom of the slidable nano-ligand presenting substrate (the opposite side of the scanning area), and the slidable nano-ligand was clearly identified in the absence of the magnet, but disappeared from the scanning area in the presence of the magnet, indicative of nanoscale nano-ligand sliding.

FIG. 9 is an image of a comparative example experiment, and is an in situ AFM image of the nano-ligand sliding in the absence of the magnet in the identical scanning. Referring to FIG. 9, black dotted lines are illustrated along the slidable nano-ligands in two different images. A scale bar indicates 50 nm. It was characterized repeatable and stable imaging in the absence of magnet near the substrate and found that the movement of the slidable nano-ligand was negligible within 4 nm displacement in the serial scanning on the identical area of the substrate.

Through this, it can be seen that it is possible to reversibly control nano-ligand sliding by spatiotemporally and reversibly alter the macroscale ligand density.

Experimental Example 3

In the method of promoting cell adhesion and regeneration of macrophages by using the slidable nano-ligand according to the present invention, the following experiment was performed to confirm the effect of controlling the density of the macroscale nano-ligand on the control of cell adhesion of the macrophages.

The binding experiment of integrin β1 to the slidable nano-ligand was carried out as described below. The substrate presenting slidable nano-ligand was used to quantify the binding efficacy of integrin β1 to the slidable nano-ligand. The substrate was immersed in integrin β1 (50 µg/mL) in phosphate-buffered saline (PBS) at 4° C. for approximately 12 hours by positioning a permanent magnet at the bottom "left" side of the substrate. The treated substrate was used for immunofluorescent staining for against integrin β1 (Santa Cruz Biotechnology) and subsequent confocal imaging to quantify integrin β1 bound to the slidable nano-ligand in situ, and a result thereof is represented in FIG. 10.

FIG. 10 is a diagram illustrating temporal modulation of integrin β1 binding of in situ control of the sliding nano-ligand. a of FIG. 10 is a schematic diagram illustrating the sliding nano-ligand with a permanent magnet positioned under the "left" side of the substrate, and b of FIG. 10 is confocal microscope images of immunofluorescence for integrin β1 clusters bound to the sliding nano-ligand at the "left", "middle", and "right" side of the substrate, which are indicated by green arrows, and in this case, a scale bar indicates 50 µm. c of FIG. 10 illustrates quantification of staining intensity of the integrin β1 clusters at the "magnet", "medium", and "non-magnet" side of the substrate. Data is displayed as mean±standard error (n=30). Statistically significant differences are indicated by different alphabet letters.

FIG. 11 is an image representing a result of the in situ control experimental of the nano-ligand sliding according to the exemplary embodiment of the present invention, and represents the promotion of adhesion of macrophages by modulating the macroscale ligand density by magnetic attraction of the slidable nano-ligand. a of FIG. 11 is schematic presentation of manipulating the slidable nano-ligand by positioning a permanent magnet at the bottom of the substrate ("magnet" side) with corresponding confocal microscope images of immunofluorescent staining against vinculin, actin, and nuclei after 24 hours of culturing macrophages subjected to a magnet placed at the bottom of the substrate ("magnet" side). The images of adherent macrophages were taken at the center of "magnet", "medium", and "non-magnet" sides of the substrate (at the red dotted rectangles in the schematic representation). A scale bar is 20 μm. Control groups include "No RGD" and "No magnet" groups. b of FIG. 11 is a graph illustrating quantification of the macrophage density, cell area, and cell aspect ratio. Data is displayed as mean±standard error (n=30). Statistical significances are indicated by different alphabet letters.

FIG. 12 is an image illustrating a result of adhesion experiment of the macrophages according to a comparative example, and a of FIG. 12 is a confocal microscope image of immunofluorescent staining of the macrophages for vinculin, F-actin, and nuclei after culturing the macrophages for 24 hours in the absence of an RGD peptide ligand or a magnetic field. The images of adherent macrophages were taken at the center of "left", "medium", and "right" sides of the substrate. A scale bar is 20 μm. b of FIG. 12 is a graph illustrating quantification of macrophage density, area, and aspect ratio. Data is displayed as mean±standard error (n=30). Statistically significant differences are indicated by different alphabet letters.

Referring to a of FIG. 10, whether the ligation of integrin 131 can be maneuvered by the slidable nano-ligand in situ was investigated, and the substrate presenting the slidable nano-ligand was incubated with integrin β1 for 12 hours whereas a permanent magnet was positioned at the bottom of the substrate ("magnet" side) Referring to b and c of FIG. 10, confocal microscope images of the immunofluorescence revealed significantly higher binding efficiency of the integrin (31 to the nano-ligand that was drawn to the magnet side of the substrate by 30% and 55%, as compared to the medium and non-magnet sides of the substrate, respectively Since integrin ligation facilitates the adhesion of macrophages, this finding suggests that macrophages could adhere more strongly to the slidable nano-ligand, which moves toward the magnet side to elevate the macroscale nano-ligand density on the magnet side. Further, in the present invention, the adhesion of macrophages under the control of the macroscale ligand density in situ was investigated.

Referring to a of FIG. 11, a magnet was positioned at the bottom of the substrate ("magnet" side) during the culturing and the adhesion of macrophages imaged at the center of "magnet", "medium", and "non-magnet" sides of the substrate was observed. Also, control experiments were conducted with the substrate presenting the slidable nano-ligand, but without the magnet ("No magnet") or the substrate with the nanoparticles without conjugated RGD peptide ligand ("No RGD").

The results showed that macrophages adhered more robustly to the "magnet" side of the substrate in significantly higher density and cell area with the pronounced actin filament assembly and vinculin expression in more elongated morphology than those adhered to the "medium" and "non-magnet" sides of the substrate. Quantitatively, the density of adherent macrophages on the "magnet" side was 59% and 82% higher than those on the "medium" and "non-magnet" sides, respectively. Similarly, the area of adherent macrophages on the "magnet" side was 57% and 60% higher than those on the "medium" and "non-magnet" sides, respectively. In addition, the aspect ratio (elongation shape factor) of adherent macrophages was 54% and 50% higher on the "magnet" side, than those on the "medium" and "non-magnet" sides, respectively.

Referring to a and b of FIG. 12, this regulation of cell adhesion of the macrophage adhesion based on the nano-ligand-sliding-mediated control was found to be inefficient for the "No RGD" and "No magnet" groups exhibiting similar adherent macrophage density and area in the "left", "middle", and "right" sides of the substrate The "No RGD" group showed minimal cell adhesion of the macrophages, thereby indicating effective blocking. These results prove that increasing macroscale ligand density with magnetic attraction of the slidable nano-ligand in situ efficiently facilitates integrin ligation-mediated adhesion of macrophages.

Experimental Example 4

An experiment about the control of reversible adhesion of macrophages by the regulation of macroscale nano-ligand density according to the present invention was conducted as described below.

Macrophages exhibit dynamic adhesion and polarization on the ECM, which is continuously being remodeled with spatially and temporally varying macroscale ligand distribution. Therefore, remote control of spatially, temporally, and reversibly varying macroscale nano-ligand distribution may emulate ECM remodeling that regulates the cell adhesion of macrophages. To this end, in the present invention, an experiment about whether temporal conversion of macroscale nano-ligand presentation by attracting the slidable nano-ligand can alter the adhesion of macrophages was conducted, and the result thereof is represented in FIGS. 13 to 15.

FIG. 13 is a diagram illustrating a result of an experiment of controlling adhesion of macrophages through the control of the macroscale nano-ligand. a of FIG. 13 is an immunofluorescent confocal microscope image against vinculin with F-actin and nuclei after 12 hours or 24 hours of culturing macrophages subjected to placing a permanent magnet at the bottom of the substrate ["magnetic field (MF)"] or withdrawing the permanent magnet from the substrate ["no magnetic field (NMF)"]. "MF" or "NMF" were applied throughout 24 hours period of culture or alternately applied after 12 hours. The images of adherent macrophages were taken at the center of "left" or "right" side of the substrate. A scale bar is 20 μm. b of FIG. 13 is a graph illustrating a calculation of the macrophage density, cell area, and cell aspect ratio for the "left" side of the substrate. Data is displayed as mean±standard error (n=30). Statistical significances are indicated by different alphabet letters.

FIG. 14 is a graph illustrating quantification of the macrophage density, cell area, and cell aspect ratio for the "right" side of the substrate in the experiment illustrated in FIG. 13. A permanent magnet was placed at the bottom "left" side of the substrate ["magnetic field (MF)"] or withdrawn from the substrate ["no magnetic field (NMF)"] during the culture of macrophages for 12 hours or 24 hours. "MF" or "NMF" were applied throughout 24 hours of culture or alternately applied after 12 hours. Data is displayed as mean±standard error (n=30). Statistically significant differences are indicated by different alphabet letters.

FIG. 15 is a time-resolved confocal microscope images of immunofluorescent staining against vinculin, actin, and nuclei after 12 hours, 24 hours, and 36 hours of culturing macrophages in the "left" and "right" sides of the substrate subjected to the switching the position of a permanent magnet between two opposite sides at the bottom "left" side of the substrate to the bottom "right" side and then to the bottom "left" side for every 12 hours. The slidable nano-ligands were imaged at the center of "left" and "right" side of the substrate (at the red dotted rectangles in the schematic diagram). A scale bar is 20 μm. b of FIG. 15 is a graph illustrating calculation of the density, cell area, and cell aspect ratio of the adherent macrophages in the "left" side of the substrate. Data is displayed as mean±standard error (n=30). Statistical significances are indicated by different alphabet letters.

Referring to FIG. 13, a permanent magnet was continuously positioned at the bottom left side of the substrate (magnetic field "MF") for 24 hours. A group without a magnet near the substrate for 24 hours was also included (No magnetic field "NMF"). Further, the present invention included a group without a magnet placed nearby for the initial 12 hours, but with the magnet placed at the bottom left side of the substrate after 12 hours ("NMF-MF"). After 24 hours, it was found that the "MF" group exhibited remarkably more pronounced macrophage adhesion, particularly higher adherent cell area by 63% and aspect ratio by 66%, on the left side (magnet side) than "NMF" group (a and b of FIG. 13). This trend was also reflected in the "NMF-MF" group that exhibited a low extent of macrophage adhesion at 12 hours without the magnet, but cell adhesion of macrophages was strikingly pronounced after 24 hours after the magnet-mediated attraction of slidable nano-ligand toward the left (magnet) side. Once the slidable nano-ligand had been attracted to the magnet (left) side, it appears to have remained even after withdrawing the magnet after 12 hours, as evidenced by maintaining macrophage adhesion after 24 hours in the "MF-NMF" group. The dramatic time-regulated switching of nano-ligand sliding was effective in regulating the cell adhesion of macrophages on the left side (magnet side), but, referring to FIG. 14, was rather ineffective in modulating the cell adhesion of macrophages on the right side (non-magnet side), thereby confirming the magnet-mediated in situ control of nano-ligand sliding.

Furthermore, in the present invention, an experiment for the effect of spatiotemporally tuning of nano-ligand sliding on the reversible adhesion of macrophages was conducted. Referring to FIG. 14, a permanent magnet was disposed at the bottom left side of the substrate to attract the slidable nano-ligand toward the left side for 12 hours. Subsequently, the position of the magnet was kept at the bottom right side of the substrate for 12 hours and then kept at the bottom left side for 12 hours. The corresponding time-resolved macrophage adhesion on the left and right side was investigated (a of FIG. 15). Referring to FIG. 15, it can be seen that the temporal regulation of the nano-ligand sliding controls reversible adhesion of macrophages. At 12 hours, the left side of the substrate showed a significantly increased adherent macrophage area by 60% and aspect ratio by 44% compared to the right side (a and b of FIG. 15). At 24 hours, the right side of the substrate showed a rather higher adherent macrophage area and aspect ratio, by 67% and 70%, respectively, than the left side. After 36 hours, reversibly, the left side of the substrate exhibited higher adherent macrophage density, cell area, and aspect ratio by 51%, 67%, and 68%, respectively, than the right side. Therefore, this remote and spatiotemporal manipulation of the macroscale nano-ligand distribution presents a powerful control in the reversible regulation of the cell adhesion of macrophages.

Experimental Example 5

In order to confirm that the slidable nano-ligand according to the present invention alters the adhesion-dependent polarization of macrophages through the time-regulated tuning, the following experiment was conducted, and a result thereof is represented in FIGS. 16 to 20.

Dynamic ECM remodeling exhibits temporally varying heterogeneous ligand distribution, which regulates the development of adhesion structures of macrophages that modulate their functional polarization phenotypes, thereby spatially and temporally regulating the host response to implants. It is known that macrophages, which develop adhesion structures with cytoskeletal actin assembly and elongated morphology, are functionally activated to the regenerative M2 phenotypes. The previous reports suggest that prior findings suggest that temporal tuning of the macroscale nano-ligand presentation may alter the adhesion-dependent polarization of macrophages.

a of FIG. 16 is a graph illustrating quantitative gene expression of M1 phenotype markers (iNOS and TNF-α) for macrophages cultured under M1-polarizing medium or M2 phenotype markers (Arginase-1 and Ym1) for macrophages cultured under M2-polarizating medium for 36 hours on the "left" and "right" side of the substrate subjected to a magnet placed at the bottom "left" side of the substrate. Data is displayed as mean±standard error (n=30). b and c of FIG. 16 are confocal microscope images of immunofluorescence against iNOS with Arg-1 and nuclei of cultured macrophages by positioning a permanent magnet at the bottom of the substrate ["magnetic field (MF)"] on the "left" side or not positioning a permanent magnet ["no magnetic field (NMF)"]. "MF" or "NMF" were applied throughout 36 hours period of culture or alternately applied after 12 hours. The images of polarized macrophages were taken at the center of "left" or "right" side of the substrate. A scale bar is 20 μm. Different alphabet letters signify statistical significances.

FIG. 17 is a graph illustrating M2 phenotype of macrophages in the M1 polarizing medium of the slidable nano-ligand according to the exemplary embodiment of the present invention. FIG. 17 illustrates ineffective control of M2 phenotype of macrophages under the slidable nano-ligand in the M1-polarizing medium. Quantitative gene expression of M2 markers (Arginase-1 and Ym1) for macrophages cultured in M2-polarizating medium on the "left" and "right" side of the substrate for 36 hours subjected to a permanent magnet placed at the bottom "left" substrate ("magnet" side). Data is displayed as mean±standard error (n=30).

FIG. 18 is a graph illustrating M1 phenotype of macrophages in the M2 polarizing medium of the slidable nano-ligand according to the exemplary embodiment of the present invention. FIG. 18 illustrates that control of M1 phenotype of macrophages under the slidable nano-ligand is inefficient in the M2-polarizing medium. FIG. 18 illustrates gene expression profiles of M1 markers (iNOS and TNF-α) for macrophages cultured in M2-polarizating medium on the "left" and "right" sides of the substrate for 36 hours subjected to a permanent magnet placed at the bottom "left" substrate ("magnet" side). Data is displayed as mean±standard error (n=30).

FIG. 19 is a confocal microscope image of immunofluorescence of an M2 phenotype experiment of macrophages for magnetic attraction of the slidable nano-ligand according to the exemplary embodiment of the present invention. Magnetic attraction of the slidable nano-ligand promotes ROCK2 expression in developing adhesion structures of macrophages to promote their M2 phenotypes. FIG. 19 is a confocal microscope image of immunofluorescence staining against ROCK2 and nuclei after culturing macrophages in a basal or M2-polarizing medium for 36 hours on the "magnet" and "non-magnet" side of the substrate subjected to a permanent magnet placed at the bottom of the substrate ("magnet" side). A scale bar is 20 μm.

FIG. 20 is a confocal microscope image of immunofluorescence (a) of a magnetic attraction regulating experiment of the nano-ligand according to the exemplary embodiment of the present invention, and b of FIG. 20 is a graph illustrating calculation of the density, cell area, and cell aspect ratio of the adherent macrophages or the area, aspect ratio, and Arg-1 staining intensity after culturing in M2 medium. Magnetic manipulation of attracting the slidable nano-ligand promotes the assembly of adhesion structures of macrophages in stimulating their M2 phenotype. a of FIG. 20 is a confocal microscope image of immunofluorescence for actin and nuclei after culturing macrophages in a basal medium for 36 hours and Arg-1 with actin and nuclei after culturing macrophages in the M2-polarizing medium for 36 hours under ROCK signal inhibition (with Y27632), myosin II forming inhibition (with blebbistatin), or actin polymerization inhibition (with cytochalasin D) on the "magnet" and "non-magnet" side of the substrate subjected to a magnet placed at the bottom of the substrate ("magnet" side). A scale bar is 20 μm. b of FIG. 20 is graph illustrating calculation of the density, cell area, and cell aspect ratio of the adherent macrophages after basal medium culture or the area, aspect ratio, and Arg-1 staining intensity after culturing in M2 medium at the "magnet" and "non-magnet" sides of the substrate. Data is displayed as mean±standard error (n=30). Statistical significances are indicated by different alphabet letters.

Referring to FIG. 16, it can be seen that the time-regulated magnetic attraction of the slidable nano-ligand suppresses the M1 phenotype of macrophages while stimulating the M2 phenotype. Phenotype presentation of the macrophages under time-regulated manipulation of the slidable nano-ligand was examined with the substrate presenting the slidable nano-ligand subjected to placing a permanent magnet at the bottom left side of the substrate ("MF" group) continuously for 36 hours, not placing a permanent near the substrate ("NMF" group) continuously for 36 hours, or switching from "NMF" to "MF" at 12 hours. After culturing macrophages in M1-polarizing medium, gene expression profiles revealed that in the "MF" group, the expression of the M1 markers iNOS (inducible nitric oxide synthase) and TNF-α (tumor necrosis factor-α) were significantly lower by 192% and 231%, respectively, on the left side (magnet side) than on the right side (non-magnet side). In contrast, after M2-polarizing medium culture in the "MF" group, the expression of M2 markers Arg-1 (arginasae-1) and Ym1 (chitinase-like 3) were significantly higher by 715% and 383%, respectively, on the left side (magnet side) than on the right side (non-magnet side). Referring to FIGS. 17 and 18, in the "MF" group, the expression of M1 markers after M2-polarizing medium culture or M2 markers after M1-polarizing medium culture, did not differ between the left and right sides, which indicates the requirement of polarizing soluble stimuli with magnetic control of nano-ligand sliding to modulate macrophage polarization.

Referring to b and c of FIG. 16, the confocal microscope images of immunofluorescence corroborated the findings of gene expression profiles. In the "MF" group, iNOS fluorescence was considerably lower after M1-polarizing medium culturing, but Arg-1 immunofluorescence was remarkably higher after M2-polarizing medium culturing on the left side (magnet side), as compared to the right side (non-magnet side). This trend was also consistent in the "NMF-MF" group exhibiting lower iNOS immunofluorescence after M1-polarizing medium culture but higher Arg-1 immunofluorescence after M2-polarizing medium culture on the magnet side, which suggests that the slidable nano-ligand may be attracted to the magnet side at any prescribed time to activate M2 polarization. In the "NMF" group, no considerable difference in iNOS and Arg-1 immunofluorescence was observed between the two sides. These findings indicate that magnetic attraction of the slidable nano-ligand, which enhanced the development of pervasive adhesion structures on the magnet side polarized the macrophages to the regenerative M2 phenotype while suppressing the inflammatory M1 polarization.

Next, an experiment was conducted on how the assembly of adherent structures in macrophages facilitates their polarization to the M2 phenotypes by the magnetic attraction of the slidable nano-ligand. Referring to FIG. 19, the adherent structures of macrophages including an elongated shape, actin cytoskeletal organization, and contractility, and ROCK are known to mediate the M2 phenotype. In basal medium and M2-polarizing medium cultures, macrophages exhibited considerably higher ROCK2 immunofluorescence on the magnet side than on the non-magnet side. Strikingly, ROCK signal inhibition with Y27632 during M2-polarizing medium culturing significantly reduced the adherent macrophage area and aspect ratio by 32% and 33%, respectively, as well as their Arg-1 immunofluorescence by 29% on the magnet side. Consistently, under myosin II forming inhibition with blebbistatin during M2-polarizing medium culturing decreased the area, aspect ratio, and Arg-1 immunofluorescence of the adherent macrophages by 33%, 31%, and 29% on the magnet side, respectively. These decreases in the area, aspect ratio, and Arg-1 fluorescence of the adherent macrophages were also clearly observed with actin polymerization inhibition by cytochalasin D. On the non-magnet side, inhibition of ROCK, myosin II, and actin polymerization did not result in significant changes in the adherent structures and production of the M2 phenotype. Taken together, these findings collectively indicate that the magnetic control of attracting slidable nano-ligand efficiently promotes the assembly of adhesion structures of macrophages in stimulating the production of the M2 phenotype.

Experimental Example 6

The following experiment was conducted in order to confirm that the slidable nano-ligand according to the present invention spatially regulates adhesion and phenotype of host macrophages in vivo through in-situ control, and a result thereof is represented in FIGS. 21 to 23.

Material implants cause host responses and it is the most important to control the adhesion and functional phenotypes of macrophages in order to elicit host responses to implants. Remote control of spatiotemporal, reversible, and macroscale nano-ligand variation may emulate dynamic and heterogenous ECM remodeling in order to spatially regulate host responses to implants. In particular, it is remarkably beneficial to regulate the cell adhesion of macrophages and production of the regenerative and anti-inflammatory M2 phenotype to mediate tissue repair while suppressing inflammation. To this end, the present invention explored the in vivo translation of the adhesion structure assembly-mediated M2 phenotype of adherent macrophages in the spatially varying regulation of the regenerative and anti-inflammatory immune responses to implants. It has recently been shown that the spatially heterogeneous modulation of macrophages adhesion by UV light is feasible. However, in the present invention, a tissue-penetrative and cytocompatible alternative using a magnetic field was used in order to regulate not only the macrophage adhesion but also the functional phenotype of adherent macrophages.

FIG. 21 is a diagram illustrating an experiment of adherent and inflammatory M1 phenotype of host macrophages in vivo against magnetic attraction of the slidable nano-ligand according to the exemplary embodiment of the present invention. a of FIG. 21 is a schematic diagram of magnetic control of the slidable nano-ligand in vivo. IL-4 and IL-13 were both injected onto the substrate presenting a slidable nano-ligand substrate after subcutaneous implantation. b of FIG. 21 is a confocal microscope image of immunofluorescence against iNOS, F-actin, and nuclei of cells adhered to the "magnet" and "non-magnet" sides of the substrate after 24 hour were analyzed. A permanent magnet was continuously placed at the bottom of the substrate ("magnet" side) for 24 hours. The images of cells were taken at the center of the "magnet" side or "non-magnet" side of the substrate. A scale bar is 20 μm. c of FIG. 21 is a graph illustrating calculation of the density, cell area, and cell aspect ratio (n=30) as well as gene expression profiles (n=3) of M1 phenotype markers (iNOS and TNF-α) of the in vivo adhered cells. Data are expressed as mean±standard error. Different alphabet letters signify statistical significances.

FIG. 22 is a diagram illustrating a result of an experiment of in vivo adhesion of host neutrophils for the slidable nano-ligand according to the exemplary embodiment of the present invention. a of FIG. 22 is a confocal microscope images of immunofluorescent staining against NIMP-R14, F-actin, and nuclei of host cells adhered to the "magnet" and "non-magnet" sides of the substrate presenting the slidable nano-ligand after 24 hours of subcutaneous implantation with an injection of IL-4 and IL-13 onto the substrate. A permanent magnet was continuously placed at the bottom of the substrate ("magnet" side) for 24 hours. The images of cells were taken at the center of "left side" or "right side" of the substrate. A scale bar is 20 μm. b of FIG. 22 is a graph illustrating quantification of the density of the in vivo adhered NIMP-R14-positive host neutrophils. Data is displayed as mean±standard error (n=30). Different alphabet letters signify statistical significances.

FIG. 23 is a diagram illustrating a result of an experiment of adhesive and regenerative M2 phenotype of host macrophages in vivo for magnetic attraction of the slidable nano-ligand according to the exemplary embodiment of the present invention. a of FIG. 23 is a confocal microscope image of immunofluorescence against Arg-1, F-actin, and nuclei of cells adhered to the "magnet" and "non-magnet" sides of the substrate presenting the slidable nano-ligand after 24 hours of subcutaneous implantation with an injection of IL-4 and IL-13 onto the substrate. A permanent magnet was continuously placed at the bottom of the substrate ("magnet" side). The images of cells were taken at the center of the "magnet" side or "non-magnet" side of the substrate. A scale bar is 20 μm. b of FIG. 23 is a graph illustrating calculation of the density, cell area, and cell aspect ratio (n=30) as well as gene expression profiles (n=3) of M2 phenotype markers (Arg-1 and Ym1) of the in vivo adhered cells.

Referring to FIG. 21, the nano-ligand-presenting substrate was used for subcutaneous implantation into balb/c mice. Following implantation, M2-polarizing soluble factors (interleukin-4 and -13) were injected onto the substrate (FIG. a of FIG. 21). A permanent magnet was attached to the bottom of the substrate ("magnet" side) on the abdomen side of the mice to promote the sliding of the nano-ligand toward the magnet side of the substrate. The substrate was collected 24 hours after implantation for confocal imaging of immunofluorescence and gene expression analysis. Confocal microscope images of immunofluorescence for iNOS and F-actin showed that pronounced colocalization was considerably more dominant on the non-magnet side than on the magnet side (b of FIG. 21). Concomitantly, more pronounced development of adhesion structures with significantly higher macrophage density, area, and aspect ratio (by 67%, 36%, and 53%, respectively) was observed on the magnet side, which promoted significantly lower expression of both iNOS and TNF by 33% and 60%, respectively, in host macrophages than on the non-magnet side (b and c of FIG. 21).

Referring to FIG. 22, not only host macrophages, but also host neutrophils were observed via NIMP-R14 immunofluorescence during the acute inflammation period. Concurrently, confocal microscope images of immunofluorescence for Arg-1 and F-actin revealed the highly pronounced assembly of adhesion structures by F-actin that positively led to colocalization with regenerative Arg-1 expression on the magnet side considerably more than on the non-magnet side. Referring to a and b of FIG. 23, this observation was also confirmed with significantly higher expression of both Arg-1 and Ym1 (regenerative M2 markers) by 27% and 60%, respectively, in the host macrophages at the magnet side, compared to the non-magnet side. Through this, it can be seen that remote control through the magnetic attraction of slidable nano-ligand promotes the regenerative M2 phenotype of host macrophages but suppresses the inflammatory M1 phenotype in vivo in a spatially regulated fashion. Tight control of early acute inflammation and regenerative responses is known to govern the long-term host responses to implants. It can be seen that it is possible to adjust immunomodulation of implants in the clinical environment through the experiment on magnetic field-mediated spatiotemporal and reversible long-term regulation in promoting tissue repair and inhibiting inflammation and fibrous capsule formation in deep interior tissues.

In the experiment example, an experiment on the adhesion and phenotype of macrophages in the culture under the in situ control of nano-ligand sliding was conducted as follows. The effect of nano-ligand sliding in vitro on the adhesion and phenotype of macrophages was examined. The substrate presenting the nano-ligand was sterilized under UV light illumination for 1 hour. The sterile substrate was subjected to blocking with 1% bovine serum albumin (BSA) for minimizing non-nano-ligand-specific adhesion of macrophages. Macrophages (RAW 264.7, passage 5, ATCC) at 50 k cells/cm$^2$ were plated on the treated substrate. Macrophages were cultured in a basal medium including high glucose DMEM supplemented with 10% (v/v) heat inactivated fetal bovine serum and 50 U/mL penicillin/streptomycin at 37° C. and 5% $CO_2$. Cells were subjected to a magnet (270 mT) placed at the bottom of the substrate ("magnet" or "left" side) and their adhesion at the center of various sides (magnet, medium, and non-magnet side) was examined. The substrates presenting nanoparticles but without RGD peptide ligand or nano-ligand but without an application of a magnet were used as control groups. The adhesion of macrophages under temporal manipulation of slidable nano-ligand was examined with a substrate presenting nano-ligand subjected to placing a permanent magnet at the bottom of the substrate ["magnetic field (MF)"] or withdrawing it from the substrate ["no magnetic field (NMF)"]. Temporal switching of a permanent magnet was also applied between two opposite sides at the bottom "left" side of the substrate to the bottom "right" side and then to the bottom "left" side back again. Polarization phenotypes of macrophages under time-regulated manipulation of the slidable nano-ligand was examined using a substrate presenting nano-ligand subjected to placing a permanent magnet at the bottom of the substrate ["magnetic field (MF)"] or withdrawing it from the substrate ["no magnetic field (NMF)"]

with their switching between "NMF" and "MF". The M1-polarizing medium included the basal medium supplemented with lipopolysaccharide (LPS, 10 ng/mL) and recombinant interferon-gamma (IFN-γ, 10 ng/mL). The M2-polarizing medium included the basal medium supplemented with interleukin-4 (IL-4, 20 ng/mL) and interleukin-13 (IL-13, 20 ng/mL). The adhesion structure assembly-mediated M2 phenotype of macrophages was examined after subjecting the substrate to a magnet placed at the bottom of the substrate ("magnet" side) under ROCK signal inhibition (with 50 μM Y27632), myosin II forming inhibition (with 10 μM blebbistatin), or actin polymerization inhibition (with 2 μg/mL cytochalasin D).

Macrophage adhesion under the slidable nano-ligand in situ by immunofluorescence and confocal imaging was analyzed as follows.

Macrophage cultures were immersed in a fixing solution of 4% (w/v) paraformaldehyde for 10 minutes, which were then washed with PBS. The cultures were incubated in a blocking buffer of 3% BSA and 0.1% Triton-X in PBS for 30 minutes. The cultures were soaked in the solution with primary antibodies against integrin (31, vinculin, iNOS, Arginase-1, ROCK2, and NIMP-R14 at 4° C. overnight, followed by washing with PBS. The cultures were immersed in the solution with secondary antibodies, phalloidin, and DAPI at room temperature for 30 minutes, followed by washing with PBS. The cultures were mounted on a microscope slide and imaged with confocal microscope (LSM700, Carl Zeiss) using the same exposure conditions for all of the compared groups, which were then examined with ImageJ software. The confocal microscope images were used to quantify the adhesion of macrophages. Integrin β1 binding intensities were calculated with histogram function. The adherent macrophage density was calculated by counting the DAPI-stained nuclei. The adherent macrophage area and aspect ratio were calculated by analyzing the F-actin staining, as reported previously.

Macrophage polarization under slidable nano-ligand in situ with reverse transcription-polymerase chain reaction was analyzed as follows.

Macrophages were cultured in M1- or M2-polarizing medium and harvested in 1 mL of Trizol per sample. The substrate was divided into two halves (magnet and non-magnet side). For each sample, 900 ng of extracted RNA was subjected to reverse transcription to cDNA by using High-Capacity RNA-to-cDNA Kit. The cDNA with Sybr Green assays was used to run real-time PCR reactions (StepOne Plus Real-Time PCR System, Applied Biosystems). The relative fold expressions of the target genes (iNOS, TNF-α, Arginase-1, and Ym1) were presented following their normalization to GAPDH expression.

Further, an experiment on in vivo remote control of the nano-ligand sliding for regulating the adhesion and phenotype of host macrophages was conducted as follows.

To investigate the effect of nano-ligand sliding in vivo on the adhesion and phenotype of host macrophages, the nano-ligand-presenting silicon substrate was used for subcutaneous implantation. 16 two month-old balb/c mice were utilized after the approval of the Institutional Animal Care and Use Committee of Korea University. The mixture of 2 mL of alfaxan and 1 mL of rompun was used for an intraperitoneal injection. The back of the mice was incised approximately in 2.5 cm length. Following implantation, IL-4 (50 ng) and IL-13 (50 ng) was injected onto the substrate. The adhesion of mouse macrophages to the substrate was tested. A permanent magnet attached to the bottom (abdomen side) of the substrate ("magnet" side) promoted the sliding of the nano-ligand toward the magnet side. At 24 hours after implantation, the substrate was retrieved for confocal imaging of the immunofluorescence and RT-PCR analysis.

What is claimed is:

1. A method of promoting cell adhesion and regeneration of macrophages, the method comprising:
   manufacturing a nano-ligand presenting substrate by putting a substrate, of which a surface is positively charged, in a solution including a nano-ligand for promoting cell adhesion and regeneration of macrophages, the nano-ligand for promoting cell adhesion and regeneration of macrophages comprising a core including magnetic nano-particles; and a coating layer provided to surround the core and including an integrin-specific ligand peptide, wherein the integrin-specific ligand peptide is negatively charged, the magnetic nano-particles comprise an iron oxide having a surface coupled with silica and have magnetic properties, and in the coating layer, the integrin-specific ligand peptide that specifically binds to an integrin of the macrophages is provided to surround an external surface of the core to coat the core; and
   controlling cell adhesion and regenerative polarization of macrophages by treating the nano-ligand presenting substrate with a culture medium and then applying an external magnetic field.

2. The method of claim 1, wherein the manufacturing of the nano-ligand presenting substrate includes:
   soaking the surface of the substrate in an acid solution;
   activating the surface of the substrate so that the surface of the substrate is positively charged by putting the soaking-completed substrate in an amino-silane solution; and
   treating the substrate, of which the surface is positively charged, by using ultrasonic waves at a room temperature.

3. The method of claim 1, wherein the substrate, of which the surface is positively charged, is activated so that the surface of the substrate exhibits positive charges by putting the substrate in the aminosilane solution.

4. The method of claim 1, wherein the controlling of the cell adhesion and the regenerative polarization of the macrophages is performed by positioning the nano-ligand presenting substrate in vivo or ex vivo and then applying a magnetic field of 100 to 700 mT for 12 to 48 hours.

5. The method of claim 1, wherein the controlling of the cell adhesion and the regenerative polarization of the macrophages is performed by changing a location of the magnetic field applied to the substrate.

6. The method of claim 1, wherein the controlling of the cell adhesion and the regenerative polarization of the macrophages is performed by changing a location of the magnetic field applied to the substrate over time.

* * * * *